US007977365B2

(12) United States Patent
Hruby et al.

(10) Patent No.: US 7,977,365 B2
(45) Date of Patent: *Jul. 12, 2011

(54) ANTIVIRAL DRUGS FOR TREATMENT OF ARENAVIRUS INFECTION

(75) Inventors: Dennis E. Hruby, Albany, OR (US); Tove C. Bolken, Keizer, OR (US); Sean Amberg, Corvallis, OR (US); Dongcheng Dai, Corvallis, OR (US); Ryan A. Larson, Corvallis, OR (US)

(73) Assignee: Siga Technologies, Inc., New York, NY (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/111,778

(22) Filed: Apr. 29, 2008

(65) Prior Publication Data

US 2008/0300265 A1 Dec. 4, 2008

Related U.S. Application Data

(63) Continuation-in-part of application No. 11/712,918, filed on Mar. 2, 2007.

(60) Provisional application No. 60/778,107, filed on Mar. 2, 2006.

(51) Int. Cl.
*A61K 31/415* (2006.01)

(52) U.S. Cl. ........ 514/394

(58) Field of Classification Search ........ 514/394
See application file for complete search history.

(56) References Cited

U.S. PATENT DOCUMENTS

| | | | |
|---|---|---|---|
| 4,492,708 | A | 1/1985 | Spitzer |
| 7,687,641 | B2 | 3/2010 | Jordan et al. |
| 2003/0134853 | A1 | 7/2003 | Priestley et al. |
| 2005/0171038 | A1 | 8/2005 | Hammond et al. |
| 2005/0187390 | A1 | 8/2005 | Schmitz et al. |
| 2007/0254934 | A1 | 11/2007 | Hruby et al. |
| 2007/0287735 | A1 | 12/2007 | Jordan et al. |
| 2008/0004452 | A1 | 1/2008 | Jordan et al. |
| 2008/0103181 | A9 | 5/2008 | Jordan et al. |
| 2009/0036513 | A1 | 2/2009 | Hruby |
| 2009/0180980 | A1 | 7/2009 | Hruby |
| 2009/0203675 | A1 | 8/2009 | Deng et al. |

FOREIGN PATENT DOCUMENTS

| | | | |
|---|---|---|---|
| WO | 0100213 | A1 | 1/2001 |
| WO | 2003099811 | A1 | 12/2003 |
| WO | WO 2005037257 | | 4/2005 |
| WO | WO 2006/062898 | | 6/2006 |

(Continued)

OTHER PUBLICATIONS

Co-pending U.S. Appl. No. 12/673,983; Inventor Dai et al.; filed Feb. 18, 2010.

(Continued)

*Primary Examiner* — Shengjun Wang
(74) *Attorney, Agent, or Firm* — Kramer Levin Naftalis & Frankel LLP

(57) ABSTRACT

Compounds, methods and pharmaceutical compositions for treating viral infections, by administering certain novel compounds in therapeutically effective amounts are disclosed. Methods for preparing the compounds and methods of using the compounds and pharmaceutical compositions thereof are also disclosed. In particular, the treatment and prophylaxis of viral infections such as caused by hemorrhagic fever viruses is disclosed, i.e., including but not limited to, Arenaviridae (Junin, Machupo, Guanarito, Sabia, Lassa, Tacaribe, Pichinde, and LCMV), Filoviridae (Ebola and Marburg viruses), Flaviviridae (yellow fever, Omsk hemorrhagic fever and Kyasanur Forest disease viruses), and Bunyaviridae (Rift Valley fever and Crimean-Congo hemorrhagic fever).

52 Claims, 4 Drawing Sheets

A

ST-37 ST-193

B

FOREIGN PATENT DOCUMENTS

| | | | |
|---|---|---|---|
| WO | WO 2007/100888 | | 9/2007 |
| WO | WO 2007/103111 | | 9/2007 |
| WO | WO 2007/120374 | | 10/2007 |
| WO | 2008079159 | A2 | 7/2008 |
| WO | 2008130348 | A1 | 10/2008 |
| WO | 2008147962 | A1 | 12/2008 |
| WO | WO 2008147474 | | 12/2008 |
| WO | 2009029622 | A2 | 3/2009 |
| WO | 2009123776 | A2 | 10/2009 |
| WO | 2009149054 | A1 | 12/2009 |

OTHER PUBLICATIONS

Office Action Dated Feb. 19, 2010, U.S. Appl. No. 11/712,918, filed Mar. 2, 2007, Inventor Hruby et al.

Office Action Dated Sep. 14, 2009, U.S. Appl. No. 10/561,153, filed Apr. 6, 2006, Inventor Jordan et al.

Office Action Dated May 6, 2007, U.S. Appl. No. 11/785,997, filed Apr. 23, 2007, Inventor Jordan et al.

Larson et al. Identification of a broad-spectrum arenavirus entry inhibitor. J. Virology Aug. 20, 2008, 82:10768-10774.

International Search Report dated Jun. 23, 2010, International Application No. PCT/US09/42031, Filing DateApr. 29, 2009.

Milata et al., "Benzazolylmethylheteroarylamines" Collection of Czechoslovak Chemical Communications, vol. 59, No. 3, 1994, pp. 725-730.

European Search Report dated Jul. 16, 2010, EP 07751991.

Beyer, W. R., D. Pöpplau, W. Garten, D. von Laer, and O. Lenz. 2003. Endoproteolytic processing of the lymphocytic choriomeningitis virus glycoprotein by the subtilase SKI-1/S1P. J Virol 77:2866-2872.

Beyer, W. R., M. Westphal, W. Ostertag, and D. von Laer. 2002. Oncoretrovifus and lentivirus vectors pseudotyped with lymphocytic choriomeningitis virus glycoprotein: generation, concentration, and broad host range. J Virol 76:1488-1495.

Borio, L., T. Inglesby, C. J. Peters, A. L. Schmaljohn, J. M. Hughes, P. B. Jahrling, T. Ksiazek, K. M. Johnson, A. Meyerhoff, T. O'Toole, M. S. Ascher, J. Bartlett, J. G. Breman, E. M. Eitzen, Jr., M. Hamburg, J. Hauer, D. A. Henderson, R. T. Johnson, G. Kwik, M. Layton, S. Lillibridge, G. J. Nabel, M. T. Osterholm, T. M. Perl, P. Russell, and K. Tonat. 2002. Hemorrhagic fever viruses as biological weapons: medical and public health management. JAMA 287:2391-2405.

Buchmeier, M. J., M. D. Bowen, and C. J. Peters. 2001. Arenaviridae: the viruses and their replication, p. 1635-1668. In D. M. Knipe and P. M. Howley (ed.), Fields virology, 4th ed. ed. Lippincott, Williams and Wilkins, Philadelphia PA.

Burns, J. W., and M. J. Buchmeier. 1991. Protein-protein interactions in lymphocytic choriomeningitis virus. Virology 183:620-629.

Cao, W., M. D. Henry, P. Borrow, H. Yamada, J. H. Elder, E. V. Ravkov, S. T. Nichol, R. W. Compans, K. P. Campbell, and M. B. A. Oldstone. 1998. Identification of α-dystroglycan as a receptor for lymphocytic choriomeningitis virus and Lassa fever virus. Science 282:2079-2081.

Centers for Disease Control and Prevention. 2004. Imported Lassa fever—New Jersey, 2004. MMWR Morb Mortal Wkly Rep 53:894-897.

Colman, P. M., and M. C. Lawrence. 2003. The structural biology of type I viral membrane fusion. Nat Rev Mol Cell Biol 4:309-319.

Connor, R. I., B. K. Chen, S. Choe, and N. R. Landau. 1995. Vpr is required for efficient replication of human immunodeficiency virus type-1 in mononuclear phagocytes. Virology 206:935-944.

Cummins, D., J. B. McCormick, D. Bennett, J. A. Samba, B. Farrar, S. J. Machin, and S. P. Fisher-Hoch. 1990. Acute sensorineural deafness in Lassa fever. JAMA 264:2093-2096.

Eichler, R., O. Lenz, T. Strecker, M. Eickmann, H.-D. Klenk, and W. Garten. 2003. Identification of Lassa virus glycoprotein signal peptide as a trans-acting maturation factor. EMBO Rep 4:1084-1088.

Eichler, R., O. Lenz, T. Strecker, M. Eickmann, H.-D. Klenk, and W. Garton. 2004. Lassa virus glycoprotein signal peptide displays a novel topology with an extended endoplasmic reticulum luminal region. J Biol Chem 279:12293-12299.

Eichler, R., O. Lenz, T. Strecker, and W. Garten. 2003. Signal peptide of Lassa virus glycoprotein GP-C exhibits an unusual length. FEBS Lett 538:203-206.

Fisher-Hoch, S. P., O. Tomori, A. Nasidi, G. I. Perez-Oronoz, Y. Fakile, L. Hutwagner, and J. B. McCormick. 1995. Review of cases of nosocomial Lassa fever in Nigeria: the high price of poor medical practice. BMJ 311:857-859.

Gallaher, W. R., C. DiSimone, and M. J. Buchmeier. 2001. The viral transmembrane superfamily: possible divergence of Arenavirus and Filovirus glycoproteins from a common RNA virus ancestor. BMC Microbiol 1:1.

Geisbert, T. W., S. Jones, E. A. Fritz, A. C. Shurtleff, J. B. Geisbert, R. Liebscher, A. Grolla, U. Ströher, L. Fernando, K. M. Daddario, M. C. Guttieri, B. R. Mothé, T. Larsen, L. E. Hensley, P. B. Jahrling, and H. Feldmann. 2005. Development of a new vaccine for the prevention of Lassa fever. PLoS Med 2:e183.

Haas, W. H., T. Breuer, G. Pfaff, H. Schmitz, P. Kohler, M. Asper, P. Emmerich, C. Drosten, U. Gölnitz, K. Fleischer, and S. Günther. 2003. Imported Lassa fever in Germany: surveillance and management of contact persons. Clin Infect Dis 36:1254-1258.

Hass, M., U. Gölnitz, S. Müller, B. Becker-Ziaja, and S. Günther. 2004. Replicon system for Lassa virus. J Virol 78:13793-13803.

Jones, S. M., H. Feldmann, U. Ströher, J. B. Geisbert, L. Fernando, A. Grolla, H.-D. Klenk, N. J. Sullivan, V. E. Volchkov, E. A. Fritz, K. M. Daddario, L. E. Hensley, P. B. Jahrling, and T. W. Geisbert. 2005. Live attenuated recombinant vaccine protects nonhuman primates against Ebola and Marburg viruses. Nat Med 11:786-790.

Kunz, S., K. H. Edelmann, J. C. de la Torre, R. Gorney, and M. B. A. Oldstone. 2003. Mechanisms for lymphocytic choriomeningitis virus glycoprotein cleavage, transport, and incorporation into virions. Virology 314:168-178.

Lenz, O., J. ter Meulen, H. D. Klenk, N. G. Seidah, and W. Garten. 2001. The Lassa virus glycoprotein precursor GP-C is proteolytically processed by subtilase SKI-1/S1P. Proc Natl Acad Sci USA 98:12701-12705.

Liao, B. S., F. M. Byl, and K. K. Adour. 1992. Audiometric comparison of Lassa fever hearing loss and idiopathic sudden hearing loss: evidence for viral cause. Otolaryngol Head Neck Surg 106:226-229.

McCormick, J. B., I. J. King, P. A. Webb, K. M. Johnson, R. O'Sullivan, E. S. Smith, S. Trippel, and T. C. Tong. 1987. A case-control study of the clinical diagnosis and course of Lassa fever. J Infect Dis 155:445-455.

McCormick, J. B., I. J. King, P. A. Webb, C. L. Scribner, R. B. Craven, K. M. Johnson, L. H. Elliott, and R. Belmont-Williams. 1986. Lassa fever. Effective therapy with ribavirin. N Engl J Med 314:20-26.

McCormick, J. B., P. A. Webb, J. W. Krebs, K. M. Johnson, and E. S. Smith. 1987. A prospective study of the epidemiology and ecology of Lassa fever. J Infect Dis 155:437-444.

Naldini, L., U. Blömer, P. Gallay, D. Ory, R. Mulligan, F. H. Gage, I. M. Verma, and D. Trono. 1996. In vivo gene delivery and stable transduction of nondividing cells by a lentiviral vector. Science 272:263-267.

NIAID. 2002. NIAID biodefense research agenda for CDC category A agents. NIH Publication No. 03-5308.

O'Brien, J., I. Wilson, T. Orton, and F. Pognan. 2000. Investigation of the Alamar Blue (resazurin) fluorescent dye for the assessment of mammalian cell cytotoxicity. Eur J Biochem 267:5421-5426.

Perez, M., R. C. Craven, and J. C. de la Torre. 2003. The small RING finger protein Z drives arenavirus budding: implications for antiviral strategies. Proc Natl Acad Sci USA 100:12978-12983.

Rotz, L. D. A. S. Khan, S. R. Lillibridge, S. M. Ostroff, and J. M. Hughes. 2002. Public health assessment of potential biological terrorism agents. Emerg Infect Dis 8:225-230.

Simmons, G., J. D. Reeves, A. J. Rennekamp, S. M. Amberg, A. J. Piefer, and P. Bates. 2004. Characterization of severe acute respiratory syndrome-associated coronavirus (SARS-CoV) spike glycoprotein-mediated viral entry. Proc Natl Acad Sci USA 101:4240-4245.

Spiropoulou, C. F., S. Kunz, P. E. Rollin, K. P. Campbell, and M. B. A. Oldstone. 2002. New World arenavirus clade C, but not clade A and B viruses, utilizes α-dystroglycan as its major receptor. J Virol 76:5140-5146.

Wool-Lewis, R. J., and P. Bates. 1998. Characterization of Ebola virus entry by using pseudotyped viruses: identification of receptor-deficient cell lines. J Virol 72:3155-3160.
World Health Organization. 2000. WHO Lassa fever fact sheet No. 179.
Goff et. al. A survey of antiviral drugs of bioweapons, Antiviral Chemistry and Chemotherapy. 2005, vol. 16, pp. 283-294.
Bolken et. al. Identification and characterization of potent small molecule inhibitor of hemorrhagic fever new world arenaviruses. Antiviral Research, Mar. 2005, vol. 65, No. 3, pp. 86-97.

A

ST-37

ST-193

B

A

B

A

B

| Mutation | ST-193 Resistance | Allele | Selection |
|---|---|---|---|
| Y 409 H | 2800 | 23B | ST-193 |
| R 412 T | 1900 | 1.10 | ST-761 |
| Q 413 H | 1850 | 9B (8/25) | ST-193 |
| Q 413 R | 580 | 5B | ST-193 |
| T 416 N | 150 | DR2 | ST-294 |
| I 418 T | 3800 | DR1 | ST-294 |
| V 421 A | 2000 | 11B | ST-193 |
| F 425 L | 30 | 9B(9/1) | ST-193 |
| F 436 I | 70 | DR4 | ST-294 |

ANTIVIRAL DRUGS FOR TREATMENT OF ARENAVIRUS INFECTION

RELATED APPLICATIONS

This application is a continuation-in-part of U.S. application Ser. No. 11/712,918, filed Mar. 2, 2007, now pending, which claims benefit of U.S. provisional application Ser. No. 60/778,107, filed Mar. 2, 2006, each of which is incorporated herein by reference.

STATEMENT REGARDING FEDERALLY SPONSORED RESEARCH OR DEVELOPMENT

This invention was made with U.S. government support under Grant No. 7R4 3AI056525 and Grant No. R44 AI056525 awarded by the National Institute of Health (NIH). The U.S. Government has certain rights in the invention.

FIELD OF THE INVENTION

The use of benzimidazole derivatives and analogs, as well as compositions containing the same, for the treatment or prophylaxis of viral diseases associated with the *arenavirus* family such as Lassa fever, Argentine hemorrhagic fever, Bolivian hemorrhagic fever, and Venezuelan hemorrhagic fever.

BACKGROUND OF THE INVENTION

Viral hemorrhagic fever is a serious illness characterized by extensive vascular damage and bleeding diathesis, fever, and multiple organ involvement. Many different viruses can cause this syndrome, each with its own animal reservoir, mode of transmission, fatality rate, and clinical outcome in humans. These viruses are distributed throughout four virus families, the Arenaviridae, Bunyaviridae, Filoviridae, and Flaviviridae. Several of these viruses generate significant morbidity and mortality and can be highly infectious by aerosol dissemination, promoting concern about weaponization. In 1999, the Centers for Disease Control and Prevention (CDC) identified and categorized potential biological terrorism agents as part of a Congressional initiative to upgrade bioterrorism response capabilities. Filoviruses and arenaviruses were designated as Category A, defined as those pathogens with the highest potential impact on public health and safety, potential for large-scale dissemination, capability for civil disruption, and greatest unmet need for public health preparedness. The National Institute of Allergy and Infectious Diseases (NIAID) has since expanded the Category A list by adding several hemorrhagic bunyaviruses and flaviviruses. In addition, the Working Group on Civilian Biodefense described several hemorrhagic fever viruses, including Lassa, as those with the greatest risk for use as biological weapons and recommended the pursuit of new antiviral therapies.

Prevention and treatment options for hemorrhagic fever viruses are limited. With the exception of an effective vaccine for yellow fever, no licensed vaccines or FDA-approved antiviral drugs are available. Intravenous ribavirin has been used with some success to treat arenaviruses and bunyaviruses, although its use has significant limitations as indicated below. In addition, there have been recent reports of promising vaccines for Ebola and Lassa. Although a successful vaccine could be a critical component of an effective biodefense, the typical delay to onset of immunity, potential side-effects, cost, and logistics associated with large-scale civilian vaccinations against a low-risk threat agent suggest that a comprehensive biodefense include a separate rapid-response element. Thus there remains an urgent need to develop safe and effective products to protect against potential biological attack.

Lassa fever virus is a member of the Arenaviridae family, a family of enveloped RNA viruses. *Arenavirus* infection in rodents, the natural host animal, is usually chronic and asymptomatic. Several arenaviruses can cause severe hemorrhagic fever in humans, including Lassa, Machupo, Guanarito, and Junin viruses. Transmission to humans can result from direct contact with infected rodents or their habitat, through aerosolized rodent secretions, or through contact with the body fluids of an infected person. Although arenaviruses are found world-wide, most of the viral species are geographically localized to a particular region, reflecting the range of the specific rodent host involved. The Arenaviridae family contains a single genus (*Arenavirus*) that is divided into two major lineages based on phylogenetic and serological examination. Lassa fever is a member of the Old World arenaviruses; the New World arenaviruses can be further divided into three clades (A-C), one of which (clade B) contains several of the pathogenic, Category A hemorrhagic fever viruses.

Lassa fever is endemic in West Africa, particularly the countries of Guinea, Liberia, Sierra Leone, and Nigeria. Human infections are estimated at 100,000 to 500,000 per year. Initial symptoms of Lassa fever appear about 10 days after exposure, and include fever, sore throat, chest and back pain, cough, vomiting, diarrhea, conjunctivitis, facial swelling, proteinuria, and mucosal bleeding. Clinical diagnosis is often difficult due to the nonspecific nature of the symptoms. In fatal cases, continuing progression of symptoms leads to the onset of shock. Among hospitalized patients, the mortality rate is 15-20%, although the fatality rate for some outbreaks has been reported higher than 50%. Infectious virus can remain in the bodily fluids of convalescent patients for several weeks. Transient or permanent deafness is common in survivors and appears to be just as frequent in mild or asymptomatic cases as it is in severe cases. Lassa fever is occasionally imported into Europe and the U.S., most recently in 2004. The risk of the virus becoming endemic outside of West Africa appears low due to the nature of the rodent host. However, the combination of increased world travel and viral adaptation presents a finite possibility of a virus "jumping" into a new ecosystem. For example, West Nile virus was introduced into the New York City area in 1999 and is now endemic in the U.S.

A small trial conducted in Sierra Leone in the 1980s demonstrated that mortality from Lassa fever can be reduced in high-risk patients by treatment with intravenous ribavirin, a nucleoside analog that exhibits nonspecific antiviral activity. Ribavirin has been shown to inhibit Lassa fever viral RNA synthesis in vitro. Although of limited availability, intravenous ribavirin is available for compassionate use under an investigational new drug protocol. It is also available in oral form for treating hepatitis C (in combination with interferon), although less is known about the efficacy of orally-administered ribavirin for treating Lassa fever. As a nucleoside analog, ribavirin can interfere with DNA and RNA replication, and in fact teratogenicity and embryo lethality have been seen in several animal species. It is therefore contraindicated for pregnant patients (a pregnancy category X drug). In addition, it is associated with a dose-related hemolytic anemia; although the anemia is reversible, anemia-associated cardiac and pulmonary events occur in approximately 10% of hepatitis C patients receiving ribavirin-interferon therapy. Intravenous ribavirin is expensive, and daily I.V. administration to a large civilian population in an emergency would be a cumbersome approach. It is possible that further study may eventually support the use of oral interferon, either alone or in combination with other antivirals, for treatment of Lassa fever. Successful antiviral therapy often involves administering a combination of pharmaceuticals, such as the treatment of chronic hepatitis C with interferon and ribavirin, and treatment of AIDS with highly active antiretroviral therapy (HAART), a cocktail of three different drugs. Because of the high mutation rate and the quasispecies nature associated with viruses, treatment with compounds that act on multiple, distinct targets can be more successful than treatment with a single drug.

The *arenavirus* genome consists of two segments of single-stranded RNA, each of which codes for two genes in opposite orientations (referred to as ambisense). The larger of the two segments, the L RNA (7.2 kb), encodes the L and Z proteins. The L protein is the RNA-dependent RNA polymerase, and the Z protein is a small zinc-binding RING finger protein which is involved in virus budding. The S RNA (3.4 kb) encodes the nucleoprotein (NP) and the envelope glycoprotein precursor (GPC).

The envelope glycoprotein is embedded in the lipid bilayer that surrounds the viral nucleocapsid. The characteristics of the *arenavirus* glycoprotein suggest that it can be classified as a Type I envelope, which is typified by influenza hemagglutinin and found also in retroviruses, paramyxoviruses, coronaviruses, and filoviruses. Type I envelopes function both to attach the virus to specific host cell receptors and also to mediate fusion of the viral membrane with the host membrane, thereby depositing the viral genome inside the target cell. Cotranslational translocation of the envelope protein across the membrane of the endoplasmic reticulum is facilitated by an N-terminal signal peptide that is subsequently removed by a signal peptidase. Post-translational proteolysis further processes the envelope into an N-terminal subunit (denoted GP1 for arenaviruses), which contains the receptor binding determinants, and a C-terminal transmembrane subunit (GP2), which is capable of undergoing the dramatic conformational rearrangements that are associated with membrane fusion. The two subunits remain associated with one another and assemble into trimeric complexes of this heterodimer. Mature envelope glycoproteins accumulate at the site of viral budding, such as the plasma membrane, and thus are embedded within the envelope that the virus acquires as viral budding occurs.

The signal peptide of the *arenavirus* glycoprotein is quite unusual; at 58 amino acids in length, it is larger than most signal peptides. In addition, it remains associated with the envelope and with mature virions, and appears to be important for the subsequent GP1-GP2 processing. This processing is essential for envelope function and is mediated by the cellular subtilase SKI-1/S1P. The envelope glycoprotein interacts directly with the host cellular receptor to facilitate viral entry into the target cell. The receptor for Old World arenaviruses is α-dystroglycan, a major component of the dystrophin glycoprotein complex. The New World arenaviruses appear to have diverged from this receptor, as only the clade C viruses use α-dystroglycan as a major receptor. The Category A hemorrhagic New World arenaviruses use transferrin receptor 1 to mediate entry into the host cell.

What is needed in the art are new therapies and preventives for the treatment of viral infections and associated diseases, such as caused by hemorrhagic fever viruses like Arenaviruses.

The following publications represent the state of the art. They are incorporated herein by reference in their entirety.

1. Beyer, W. R., D. Pöpplau, W. Garten, D. von Laer, and O. Lenz. 2003. Endoproteolytic processing of the lymphocytic choriomeningitis virus glycoprotein by the subtilase SKI-1/S1P. J Virol 77:2866-2872.
2. Beyer, W. R., M. Westphal, W. Ostertag, and D. von Laer. 2002. Oncoretrovirus and lentivirus vectors pseudotyped with lymphocytic choriomeningitis virus glycoprotein: generation, concentration, and broad host range. J Virol 76:1488-1495.
3. Borio, L., T. Inglesby, C. J. Peters, A. L. Schmaljohn, J. M. Hughes, P. B. Jahrling, T. Ksiazek, K. M. Johnson, A. Meyerhoff, T. O'Toole, M. S. Ascher, J. Bartlett, J. G. Breman, E. M. Eitzen, Jr., M. Hamburg, J. Hauer, D. A. Henderson, R. T. Johnson, G. Kwik, M. Layton, S. Lillibridge, G. J. Nabel, M. T. Osterholm, T. M. Perl, P. Russell, and K. Tonat. 2002. Hemorrhagic fever viruses as biological weapons: medical and public health management. JAMA 287:2391-2405.
4. Buchmeier, M. J., M. D. Bowen, and C. J. Peters. 2001. Arenaviridae: the viruses and their replication, p. 1635-1668. In D. M. Knipe and P. M. Howley (ed.), Fields virology, 4th ed. ed. Lippincott, Williams and Wilkins, Philadelphia Pa.
5. Eschli, B., K. Quirin, A. Wepf, J. Weber, R. Zinkernagel, and H. Hengartner. 2006. Identification of an N-terminal trimeric coiled-coil core within *arenavirus* glycoprotein 2 permits assignment to class I viral fusion proteins. J. Virol. 80:5897-5907.
6. Cao, W., M. D. Henry, P. Borrow, H. Yamada, J. H. Elder, E. V. Ravkov, S. T. Nichol, R. W. Compans, K. P. Campbell, and M. B. A. Oldstone. 1998. Identification of α-dystroglycan as a receptor for lymphocytic choriomeningitis virus and Lassa fever virus. Science 282:2079-2081.
7. Centers for Disease Control and Prevention. 2004. Imported Lassa fever—New Jersey, 2004. MMWR Morb Mortal Wkly Rep 53:894-897.
8. Colman, P. M., and M. C. Lawrence. 2003. The structural biology of type I viral membrane fusion. Nat Rev Mol Cell Biol 4:309-319.
9. Connor, R. I., B. K. Chen, S. Choe, and N. R. Landau. 1995. Vpr is required for efficient replication of human immunodeficiency virus type-1 in mononuclear phagocytes. Virology 206:935-944.
10. Cummins, D., J. B. McCormick, D. Bennett, J. A. Samba, B. Farrar, S. J. Machin, and S. P. Fisher-Hoch. 1990. Acute sensorineural deafness in Lassa fever. JAMA 264:2093-2096.
11. Eichler, R., O. Lenz, T. Strecker, M. Eickmann, H.-D. Kienk, and W. Garten. 2003. Identification of Lassa virus glycoprotein signal peptide as a trans-acting maturation factor. EMBO Rep 4:1084-1088.
12. Eichler, R., O. Lenz, T. Strecker, M. Eickmann, H.-D. Kienk, and W. Garten. 2004. Lassa virus glycoprotein signal peptide displays a novel topology with an extended endoplasmic reticulum luminal region. J Biol Chem 279: 12293-12299.
13. Eichler, R., O. Lenz, T. Strecker, and W. Garten. 2003. Signal peptide of Lassa virus glycoprotein GP-C exhibits an unusual length. FEBS Lett 538:203-206.
14. Fisher-Hoch, S. P., O. Tomori, A. Nasidi, G. I. Perez-Oronoz, Y. Fakile, L. Hutwagner, and J. B. McCormick. 1995. Review of cases of nosocomial Lassa fever in Nigeria: the high price of poor medical practice. BMJ 311:857-859.
15. Gallaher, W. R., C. DiSimone, and M. J. Buchmeier. 2001. The viral transmembrane superfamily: possible divergence of *Arenavirus* and Filovirus glycoproteins from a common RNA virus ancestor. BMC Microbiol 1:1.
16. Geisbert, T. W., S. Jones, E. A. Fritz, A. C. Shurtleff, J. B. Geisbert, R. Liebscher, A. Grolla, U. Ströher, L. Fernando, K. M. Daddario, M. C. Guttieri, B. R. Mothe, T. Larsen, L. E. Hensley, P. B. Jahrling, and H. Feldmann. 2005. Development of a new vaccine for the prevention of Lassa fever. PLoS Med 2:e183.
17. Haas, W. H., T. Breuer, G. Pfaff, H. Schmitz, P. Kohler, M. Asper, P. Emmerich, C. Drosten, U. Gölnitz, K. Fleischer, and S. Günther. 2003. Imported Lassa fever in Germany: surveillance and management of contact persons. Clin Infect Dis 36:1254-1258.
18. Hass, M., U. Gölnitz, S. Müller, B. Becker-Ziaja, and S. Günther. 2004. Replicon system for Lassa virus. J Virol 78:13793-13803.
19. Jones, S. M., H. Feldmann, U. Ströher, J. B. Geisbert, L. Fernando, A. Grolla, H.-D. Kienk, N. J. Sullivan, V. E. Volchkov, E. A. Fritz, K. M. Daddario, L. E. Hensley, P. B. Jahrling, and T. W. Geisbert. 2005. Live attenuated recombinant vaccine protects nonhuman primates against Ebola and Marburg viruses. Nat Med 11:786-790.
20. Kunz, S., K. H. Edelmann, J. C. de la Torre, R. Gorney, and M. B. A. Oldstone. 2003. Mechanisms for lymphocytic choriomeningitis virus glycoprotein cleavage, transport, and incorporation into virions. Virology 314:168-178.
21. Lenz, O., J. ter Meulen, H. D. Kienk, N. G. Seidah, and W. Garten. 2001. The Lassa virus glycoprotein precursor GP-C is proteolytically processed by subtilase SKI-1/S1P. Proc Natl Acad Sci USA 98:12701-12705.
22. Liao, B. S., F. M. Byl, and K. K. Adour. 1992. Audiometric comparison of Lassa fever hearing loss and idiopathic sudden hearing loss: evidence for viral cause. Otolaryngol Head Neck Surg 106:226-229.
23. McCormick, J. B., I. J. King, P. A. Webb, K. M. Johnson, R. O'Sullivan, E. S. Smith, S. Trippel, and T. C. Tong. 1987. A case-control study of the clinical diagnosis and course of Lassa fever. J Infect Dis 155:445-455.
24. McCormick, J. B., I. J. King, P. A. Webb, C. L. Scribner, R. B. Craven, K. M. Johnson, L. H. Elliott, and R. Belmont-Williams. 1986. Lassa fever. Effective therapy with ribavirin. N Engl J Med 314:20-26.
25. McCormick, J. B., P. A. Webb, J. W. Krebs, K. M. Johnson, and E. S. Smith. 1987. A prospective study of the epidemiology and ecology of Lassa fever. J Infect Dis 155:437-444.
26. Naldini, L., U. Blömer, P. Gallay, D. Ory, R. Mulligan, F. H. Gage, I. M. Verma, and D. Trono. 1996. In vivo gene delivery and stable transduction of nondividing cells by a lentiviral vector. Science 272:263-267.
27. NIAID. 2002. NIAID biodefense research agenda for CDC category A agents. NIH Publication No. 03-5308.
28. O'Brien, J., I. Wilson, T. Orton, and F. Pognan. 2000. Investigation of the Alamar Blue (resazurin) fluorescent dye for the assessment of mammalian cell cytotoxicity. Eur J Biochem 267:5421-5426.
29. Perez, M., R. C. Craven, and J. C. de la Torre. 2003. The small RING finger protein Z drives *arenavirus* budding: implications for antiviral strategies. Proc Natl Acad Sci USA 100:12978-12983.
30. Radoshitzky, S. R., J. Abraham, C. F. Spiropoulou, J. H. Kuhn, D. Nguyen, W. Li, J. Nagel, P. J. Schmidt, J. H. Nunberg, N.C. Andrews, M. Farzan, and H. Choe. 2007. Transferrin receptor 1 is a cellular receptor for New World haemorrhagic fever arenaviruses. Nature 446:92-96.
31. Rotz, L. D., A. S. Khan, S. R. Lillibridge, S. M. Ostroff, and J. M. Hughes. 2002. Public health assessment of potential biological terrorism agents. Emerg Infect Dis 8:225-230.
32. Simmons, G., J. D. Reeves, A. J. Rennekamp, S. M. Amberg, A. J. Piefer, and P. Bates. 2004. Characterization of severe acute respiratory syndrome-associated coronavirus (SARS-CoV) spike glycoprotein-mediated viral entry. Proc Natl Acad Sci USA 101:4240-4245.
33. Spiropoulou, C. F., S. Kunz, P. E. Rollin, K. P. Campbell, and M. B. A. Oldstone. 2002. New World *arenavirus* clade C, but not clade A and B viruses, utilizes α-dystroglycan as its major receptor. J Virol 76:5140-5146.
34. Wool-Lewis, R. J., and P. Bates. 1998. Characterization of Ebola virus entry by using pseudotyped viruses: identification of receptor-deficient cell lines. J Virol 72:3155-3160.
35. World Health Organization. 2000. WHO Lassa fever fact sheet No. 179.

SUMMARY OF THE INVENTION

Provided are compounds and compositions and/or methods for the treatment and prophylaxis of viral infections, as well as diseases associated with viral infections in living hosts. In particular, provided are compounds and compositions and/or methods for the treatment and prophylaxis of hemorrhagic fever viruses, such as Arenaviruses.

In an embodiment, a method for the treatment or prophylaxis of a viral infection or disease associated therewith, comprising administering in a therapeutically effective amount to a mammal in need thereof, a compound of Formula I or a pharmaceutically acceptable salt thereof is provided. In another embodiment, a pharmaceutical composition that comprises a pharmaceutically-effective amount of the compound or a pharmaceutically-acceptable salt thereof, and a pharmaceutically-acceptable carrier is provided. In addition, compounds of Formula I, as well as pharmaceutically-acceptable salts thereof are provided.

The compounds of Formula I are of the following general formula:

I

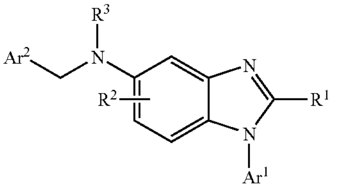

Wherein $R^1$ and $R^2$ are independently hydrogen, alkyl, alkenyl, alkynyl, cycloalkyl, arylalkyl, aryl, acyl, arylacyl, hydroxy, alkyloxy, alkylthio, amino, alkylamino, acetamido, halogen, cyano or nitro;

$R^3$ is hydrogen, acyl, arylacyl or sulfonyl; and $Ar^1$ and $A^2$ are independently (un)substituted aryl or heteroaryl.

In an embodiment, the mammal being treated is a human. In particular embodiments, the disease being treated is caused by a viral infection, such as by an *Arenavirus*. The *Arenavirus* may be selected from the group consisting of Lassa, Junin, Machupo, Guanarito, Sabia, Whitewater Arroyo, Chapare, LCMV, LCMV-like viruses such as Dandenong, Tacaribe, and Pichinde.

Details of methods and formulations are more fully described below. Other objects and advantages of the present invention will become apparent from the following description and appended claims.

DETAILED DESCRIPTION

Figure 1A:
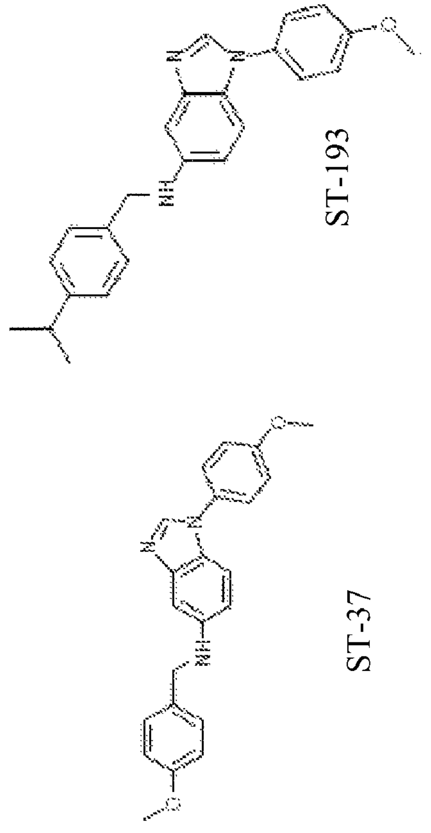
FIGS. 1A and 1B show the structure and antiviral activity of ST-37 and ST-193. (1A) Benzimidazole derivative ST-37 (left) was modified to generate ST-193 (right). (1B) Inhibition of LASV GP- or VSVg-pseudotyped HIV infection with ST-37 or ST-193. Infectivity measured by luciferase reporter relative to controls with no compound. Each point is an average of three replicates, with error bars designating standard deviation.

Compounds which are useful for the treatment and prophylaxis of viral infections, particularly arenaviral infections, including diseases associated with arenaviral infections in living hosts, are provided. In particular, provided are compounds and compositions and/or methods for the treatment and prophylaxis of hemorrhagic fever viruses, such as Arenaviruses. However, prior to providing further detail, the following terms will first be defined.

Definitions

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, experimental animals including rats, mice, and guinea pigs, domestic and farm animals, and zoo, sports, or pet animals, such as dogs, horses, cats, cows, and the like.

The term "efficacy" as used herein in the context of a chronic dosage regime refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C (O)—, aryl-C(O)—, substituted aryl-C(O)—, heteroaryl-C (O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkylamino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Amino" refers to the group —$NH_2$.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one, and the like) provided that the point of attachment is through an aromatic ring atom.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$— substituted heterocyclic, —$OS(O)_2$—NRR where R is hydrogen, or alkyl, —$NRS(O)_2$— alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —NRS $(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Halo" or "halogen" refers to fluoro, chloro, bromo and iodo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (═O). The term "heteroaryl having two nitrogen atoms in the heteroaryl, ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$ -cycloalkyl, —$S(O)_2$-substituted cycloalkyl, —$S(O)_2$ -alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$—heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2$NRR where R is hydrogen or alkyl.

"Sulfonyl" refers to the group —$S(O)_2$R where R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. A pharmaceutically-acceptable carrier or excipient includes both one or more than one of such carriers.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable. Pharmaceutically-acceptable salts refer to pharmaceutically-acceptable salts of the compounds, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Prodrugs are prepared by modifying functional groups present in such a way that the modifications may be cleaved in vivo to release the parent compound. Prodrugs include compounds wherein a hydroxy, amino, or sulfhydryl group is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl) of hydroxy functional groups, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically-effective amount" means the amount of a compound or antibody that, when administered to a mammal for treating a disease, is sufficient to effect such treatment for the disease. The "therapeutically-effective amount" will vary depending on the compound, the disease, and its severity and the age, weight, etc., of the mammal to be treated.

Provided are compounds and compositions and/or methods for the treatment and prophylaxis of viral infections, as well as diseases associated with viral infections in living hosts. In particular, provided are compounds and compositions and/or methods for the treatment and prophylaxis of hemorrhagic fever viruses, such as Arenaviruses.

In an embodiment, a method for the treatment or prophylaxis of a viral infection or disease associated therewith, comprising administering in a therapeutically effective amount to a mammal in need thereof, a compound of Formula I or a pharmaceutically acceptable salt thereof is provided. In another embodiment, a pharmaceutical composition that comprises a pharmaceutically-effective amount of the compound or a pharmaceutically-acceptable salt thereof, and a pharmaceutically-acceptable carrier is provided. In addition, compounds of Formula I, as well as pharmaceutically-acceptable salts thereof are provided.

The compounds of Formula I are of the following general formula:

I

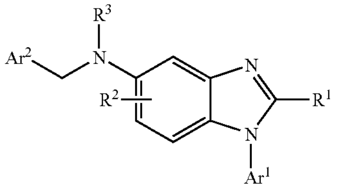

Wherein $R^1$ and $R^2$ are independently hydrogen, alkyl, alkenyl, alkynyl, cycloalkyl, arylalkyl, aryl, acyl, arylacyl, hydroxy, alkyloxy, alkylthio, amino, alkylamino, acetamido, halogen, cyano or nitro;

$R^3$ is hydrogen, acyl, arylacyl or sulfonyl; and $Ar^1$ and $Ar^2$ are independently (un)substituted aryl or heteroaryl Exemplary compounds of Formula I are shown below in Table 1:

TABLE I

| Exemplary compounds of Formula I | | |
|---|---|---|
| No. | formula | structure/name |
| 600037 | $C_{22}H_{21}N_3O_2$ | 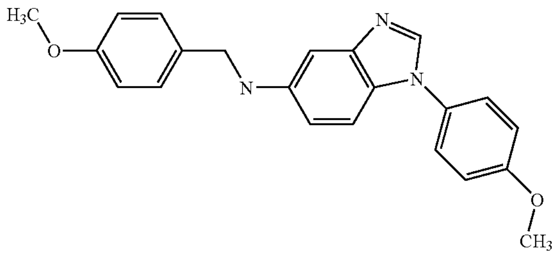 (4-methoxy-benzyl)-[1-(4-methoxy-phenyl)-1H-benzimidazol-5-yl]-amine |
| 600137 | $C_{23}H_{24}N_4O$ | 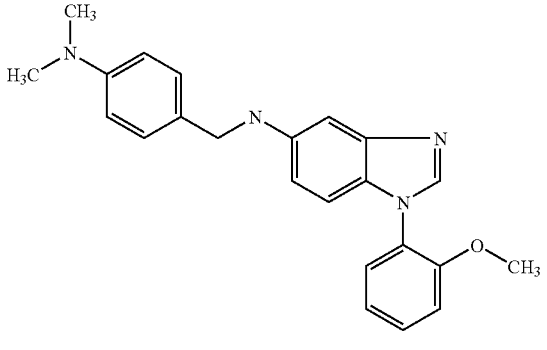 (4-dimethylamino- |

TABLE I-continued
| No. | formula | structure/name |
|---|---|---|
| | | benzyl)-[1-(2-methoxy-phenyl)-1H-benzimidazol-5-yl]-amine |
| 600144 | $C_{22}H_{22}N_4$ | 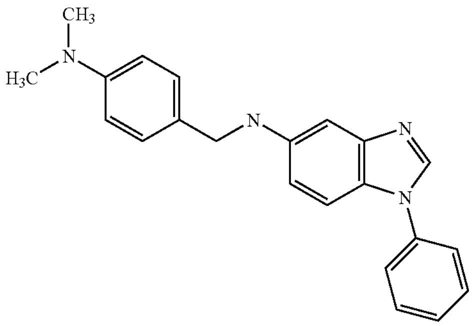 (4-dimethylamino-benzyl)-[1-phenyl-1H-benzimidazol-5-yl]-amine |
| 600145 | $C_{21}H_{18}N_3OBr$ | 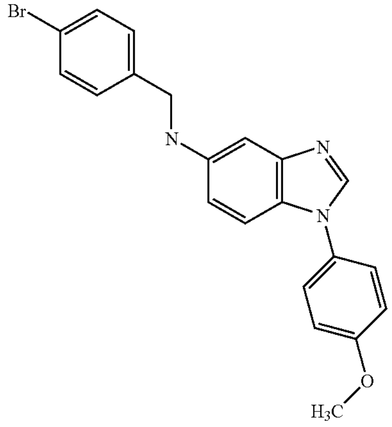 (4-bromo-benzyl)-[1-(4-methoxy-phenyl)-1H-benzimidazol-5-yl]-amine |
| 600146 | $C_{22}H_{21}N_3O_2$ | 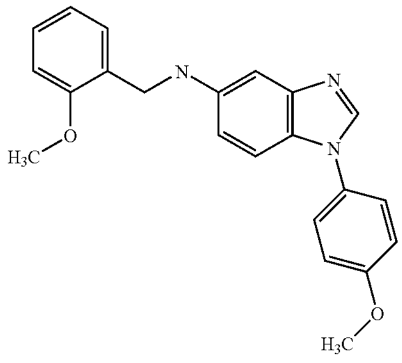 (2-methoxy-benzyl)-[1-(4-methoxy-phenyl)-1H-benzimidazol-5-yl]-amine |
(Table header: Exemplary compounds of Formula I)

TABLE I-continued
| No. | formula | structure/name |
| --- | --- | --- |
| | | Exemplary compounds of Formula I |
| 600147 | $C_{23}H_{23}N_3O_2$ | 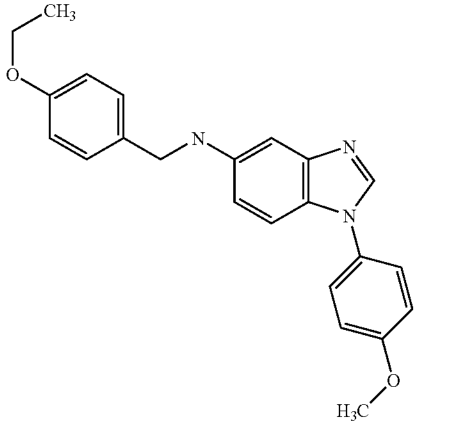 (4-ethoxy-benzyl)-[1-(4-methoxy-phenyl)-1H-benzimidazol-5-yl]-amine |
| 600148 | $C_{22}H_{21}N_3O_2$ | 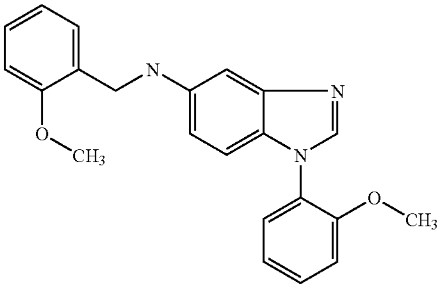 (2-methoxy-benzyl)-[1-(4-methoxy-phenyl)-1H-benzimidazol-5-yl]-amine |
| 600149 | $C_{25}H_{21}N_3O$ | 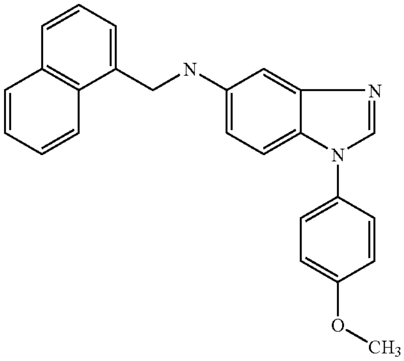 [1-(4-methoxy-phenyl)-1H-benzimidazol-5-yl]-napthalen-1-ylmethyl-amine |
| 600153 | $C_{21}H_{19}N_3O_2$ | 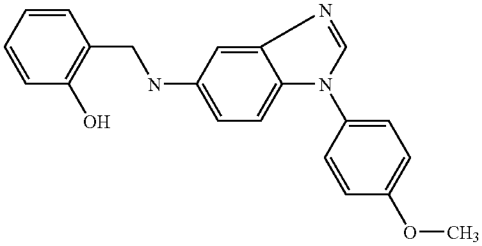 |

TABLE I-continued
| Exemplary compounds of Formula I | | |
|---|---|---|
| No. | formula | structure/name |
| | | 2-[[1-(4-methoxy-phenyl)-1H-benzimidazol-5-ylamino]-methyl]-phenol |
| 600169 | $C_{22}H_{21}N_3O$ | 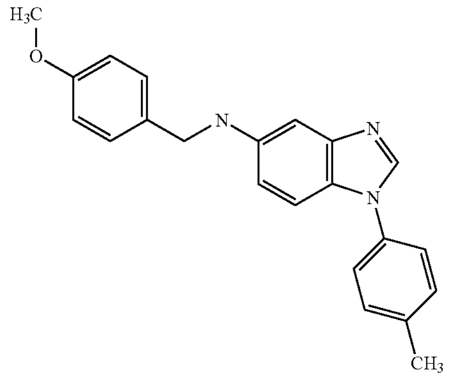<br>(4-methoxy-benzyl)-(1-p-tolyl-1H-benzimidazol-5-yl)-amine |
| 600170 | $C_{22}H_{18}N_3OCl$ | 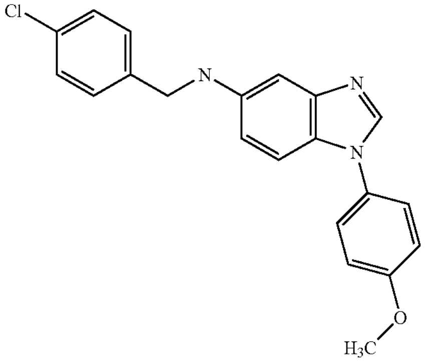<br>(4-chloro-benzyl)-[1-(4-methoxy-phenyl)-1H-benzimidazol-5-yl]-amine |
| 600172 | $C_{23}H_{23}N_3O_3$ | 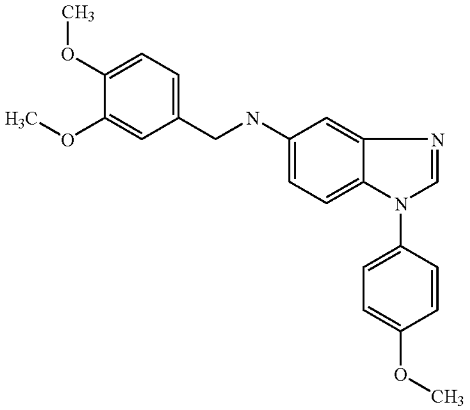<br>(3,4-dimethoxy-benzyl)-[1-(4-methoxy-phenyl)-1H-benzimidazol-5-yl]-amine |

TABLE I-continued
| Exemplary compounds of Formula I | | |
|---|---|---|
| No. | formula | structure/name |
| 600173 | $C_{20}H_{16}N_3Br$ | 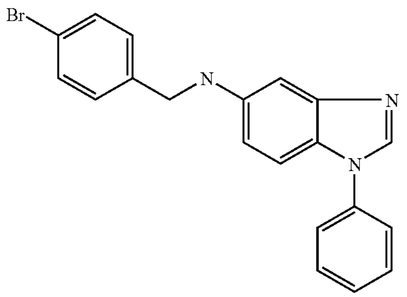 (4-bromo-benzyl)-(1-phenyl-1H-benzimidazol-5-yl)-amine |
| 600179 | $C_{30}H_{29}N_3O_4S$ | 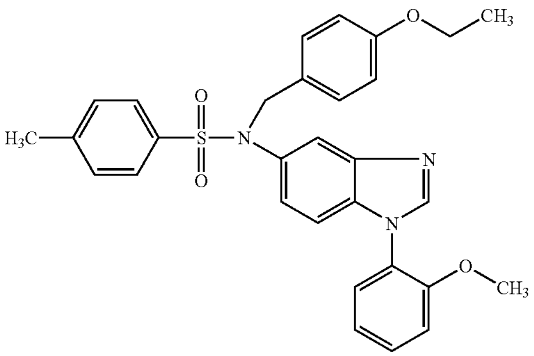 N-(4-ethoxy-benzyl)-N-[1-(2-methoxy-phenyl)-1H-benzimidazol-5-yl]-4-methylbenzenesulfonamide |
| 600188 | $C_{22}H_{21}N_3O$ | 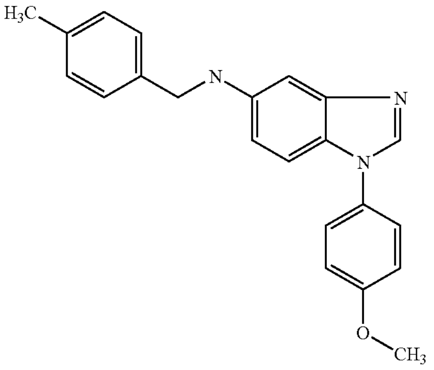 [1-(4-methoxy-phenyl)-1H-benzimidazol-5-yl]-(4-methyl-benzyl)-amine |

TABLE I-continued
| Exemplary compounds of Formula I | | |
|---|---|---|
| No. | formula | structure/name |
| 600189 | $C_{23}H_{23}N_3O_3$ | 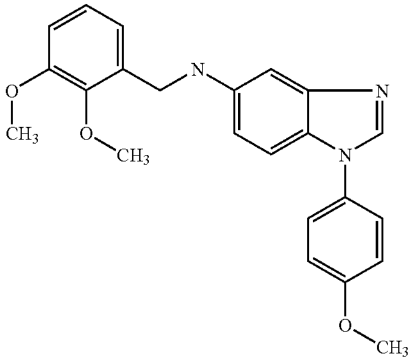 (2,3-dimethoxy-benzyl)-[1-(4-methoxy-phenyl)-1H-benzimidazol-5-yl]-amine |
| 600190 | $C_{22}H_{21}N_3O_2$ | 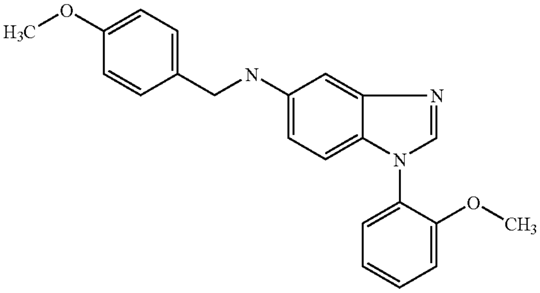 (4-methoxy-benzyl)-[1-(2-methoxy-phenyl)-1H-benzimidazol-5-yl]-amine |
| 600191 | $C_{22}H_{21}N_3O_2$ | 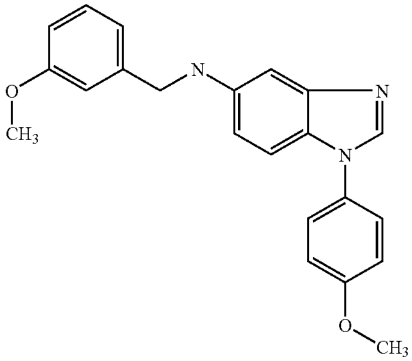 (3-methoxy-benzyl)-[1-(4-methoxy-phenyl)-1H-benzimidazol-5-yl]-amine |

TABLE I-continued
| Exemplary compounds of Formula I | | |
|---|---|---|
| No. | formula | structure/name |
| 600192 | $C_{23}H_{23}N_3O_3$ | 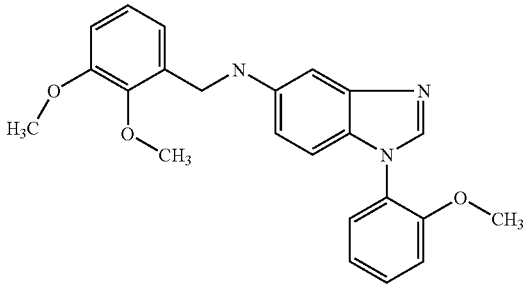 (2,3-dimethoxy-benzyl)-[1-(2-methoxy-phenyl)-1H-benzimidazol-5-yl]-amine |
| 600193 | $C_{24}H_{25}N_3O$ | 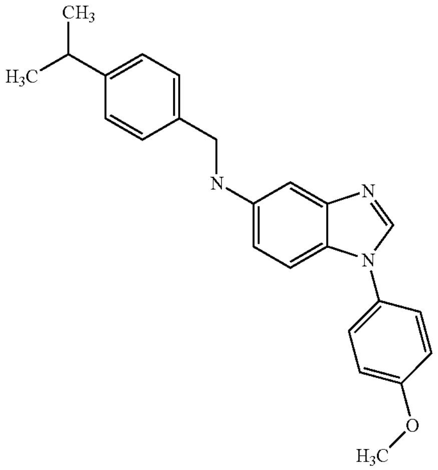 (4-isopropyl-benzyl)-[1-(4-methoxy-phenyl)-1H-benzimidazol-5-yl]-amine |
| 600196 | $C_{21}H_{19}N_3O$ | 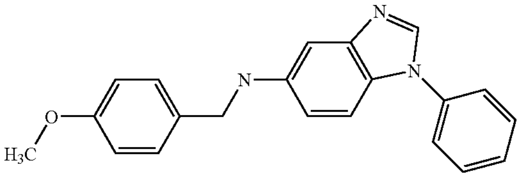 (4-methoxy-benzyl)-(1-phenyl-1H-benzimidazol-5-yl)-amine |
| 600362 | $C_{26}H_{27}N_3O_2$ | 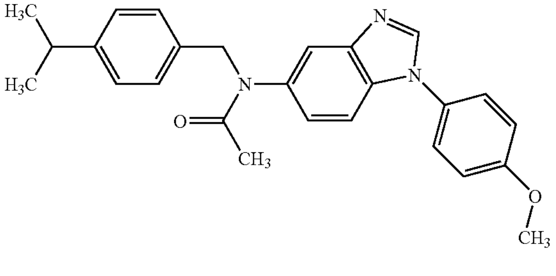 N-(4-isopropyl-benzyl)-N-[1-4-methoxy-phenyl)-1H-benzimidazol-5-yl]-acetamide |

TABLE I-continued

| Exemplary compounds of Formula I | | |
|---|---|---|
| No. | formula | structure/name |
| 600363 | $C_{31}H_{31}N_3O_3S$ | 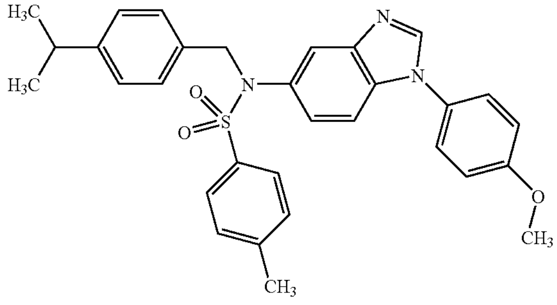 N-(4-isopropyl-benzyl)-N-[1-(4-methoxy-phenyl)-1H-benzimidazol-5-yl]-4-methylbenzenesulfonamide |

In an embodiment, the mammal being treated is a human. In particular embodiments, the disease being treated is caused by a viral infection, such as by an *Arenavirus*. The *Arenavirus* may be selected from the group consisting of Lassa, Junin, Machupo, Guanarito, Sabia, Whitewater Arroyo, Chapare, LCMV, LCMV-like viruses such as Dandenong, Tacaribe, and Pichinde.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of 24 pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffenalendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

A useful buffer is sodium citrate/citric acid in the range of 5 to 50 mg per ml, sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the compounds, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly (vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host.

Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

The provided compounds and pharmaceutical compositions show biological activity in treating and preventing viral infections and associated diseases, and, accordingly, have utility in treating viral infections and associated diseases, such as Hemorrhagic fever viruses, in mammals including humans.

Hemorrhagic fever viruses (HFVs) are RNA viruses that cause a variety of disease syndromes with similar clinical characteristics. HFVs that are of concern as potential biological weapons include but are not limited to: Arenaviridae (Junin, Machupo, Guanarito, Sabia, and Lassa), Filoviridae (Ebola and Marburg viruses), Flaviviridae (yellow fever, Omsk hemorrhagic fever and Kyasanur Forest disease viruses), and Bunyaviridae (Rift Valley fever and Crimean-Congo hemorrhagic fever). The naturally-occurring arenaviruses and potential engineered arenaviruses are included in the Category A Pathogen list according to the Centers for Disease Control and Prevention as being among those agents that have greatest potential for mass casualties.

Risk factors include: travel to Africa or Asia, handling of animal carcasses, contact with infected animals or people, and/or arthropod bites. Arenaviruses are highly infectious after direct contact with infected blood and/or bodily secretions. Humans usually become infected through contact with infected rodents, the bite of an infected arthropod, direct contact with animal carcasses, inhalation of infectious rodent excreta and/or injection of food contaminated with rodent excreta. The Tacaribe virus has been associated with bats. Airborne transmission of hemorrhagic fever is another mode. Person-to-person contact may also occur in some cases.

All of the hemorrhagic fevers exhibit similar clinical symptoms. However, in general the clinical manifestations are non-specific and variable. The incubation period is approximately 7-14 days. The onset is gradual with fever and malaise, tachypnea, relative bradycardia, hypotension, circulatory shock, conjunctival infection, pharyngitis, lymphadenopathy, encephalitis, myalgia, back pain, headache and dizziness, as well as hyperesthesia of the skin. Some infected patients may not develop hemorrhagic manifestations.

Methods of diagnosis at specialized laboratories include antigen detection by antigen-capture enzyme-linked immunosorbent assay (ELISA), IgM antibody detection by antibody-capture enzyme-linked immunosorbent assay, reverse transcriptase polymerase chain reaction (RT-PCR), and viral isolation. Antigen detection (by enzyme-linked immunosorbent assay) and reverse transcriptase polymerase chain reaction are the most useful diagnostic techniques in the acute clinical setting. Viral isolation is of limited value because it requires a biosafety level 4 (BSL-4) laboratory.

EXAMPLE 1

Synthesis of Compounds

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

The compounds are readily prepared via several divergent synthetic routes with the particular route selected relative to the ease of compound preparation, the commercial availability of starting materials, and the like.

The compounds can be prepared from readily-available starting materials using the following general methods and procedures. It will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included unless otherwise indicated. Pure stereoisomers (or enriched mixtures) may be prepared using, for example, optically-active starting materials or stereoselective reagents well-known in the art. Alternatively, racemic mixtures of such compounds can be separated using, for example, chiral column chromatography, chiral resolving agents, and the like.

Unless otherwise indicated, the products are a mixture of R, S enantiomers. However, when a chiral product is desired, the chiral product can be obtained via purification techniques which separate enantiomers from a R, S mixture to provide for one or the other stereoisomer. Such techniques are known in the art.

In another embodiment, the compounds can be provided as pro-drugs which convert (e.g., hydrolyze, metabolize, etc.) in vivo to a compound above.

In the examples below, if an abbreviation is not defined above, it has its generally accepted meaning. Further, all temperatures are in degrees Celsius (unless otherwise indicated). The following Methods were used to prepare the compounds set forth below as indicated.

General Synthetic Procedure

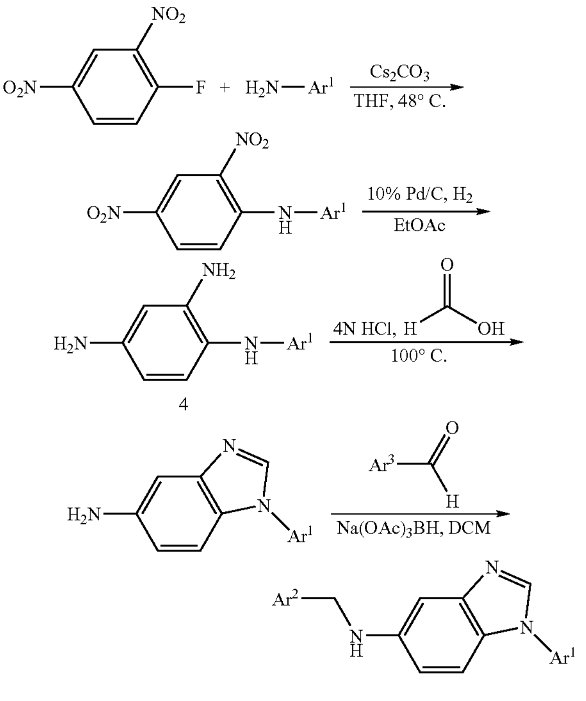

4

Step 1: To a solution of dinitrofluorobenzene (251 μl, 2 mmol) in THF (2 ml) was added cesium carbonate (780 mg, 2.4 mmol) and aniline ($H_2N$—$Ar^1$, 2 mmol). The mixture was heated to 48° C. overnight. The reaction was cooled to room temperature and filtered through a pre-packed 5 g silica cartridge and eluted with EtOAc (~15 ml). The solvent was removed in vacuo and the crude material was carried forward without purification.

Step 2: To a solution of crude starting material from step 1 in EtOAc was added a scoop of 10% Pd/C (~50 mg). The vial was sealed, flushed with Argon, and then placed under $H_2$ balloon. The mixture was stirred at room temperature overnight. The reaction mixture was filtered through a pad of Celite and eluted with EtOAc. The solvent was removed in vacuo and crude material was carried forward without purification.

Step 3: The crude material from step 2 was suspended in 4N HCl (2 ml) and formic acid (0.5 ml). The mixture was heated to 100° C. for 1.5 hours. The reaction was cooled to room temperature and 5 N NaOH was added to adjust pH to 13. The mixture was extracted with DCM (3×5 ml). The combined organic layers were dried over $MgSO_4$, filtered, and solvent evaporated in vacuo to give the crude product that was carried forward without purification.

Step 4: To a solution of crude starting material from step 3 in DCM (3 ml) was added aldehyde ($Ar^2$—CHO, 2 mmol) and $Na(AcO)_3BH$ (630 mg, 3 mmol). The reaction was stirred at room temperature for 1.5 hours (when reaction was complete by TLC). The crude reaction mixture was filtered and loaded onto a 40 g RediSep silica-gel cartridge and eluted with a gradient of EtOAc in hexanes to yield the final product. The identity was confirmed by LC-MS and $^1H$ NMR and purity confirmed by HPLC.

Synthesis of (4-isopropyl-benzyl)-[1-(4-methoxy-phenyl)-1H-benzimidazol-5-yl]-amine

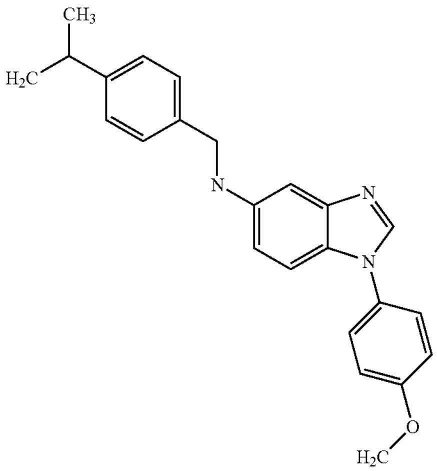

The compound was synthesized according to the General Procedure described above. $^1H$ NMR (300 MHz, $CDCl_3$): δ 7.94 (s, 1H), 7.39 (m, 4H), 7.24 (m, 4H), 7.04 (m, 3H), 6.74 (dd, 1H), 4.38 (s, 2H), 3.90 (s, 3H), 2.93 (septet, 1H), 1.27 (d, 6H). $^{13}C$ NMR (75 MHz, $CDCl_3$): δ 159.04, 147.92, 145.19, 144.95, 142.03, 136.80, 129.57, 127.71, 127.43, 126.69, 125.31, 115.04, 112.73, 110.74, 101.83, 55.64, 48.99, 33.83, 24.05.

EXAMPLE 2

Formulation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

EXAMPLE 3

Formulation 2

A tablet formula is prepared using the ingredients below:

| Ingredient | Quantity (mg/capsule) |
|---|---|
| Active ingredient | 25.0 |
| Cellulose, microcrystalline | 200.0 |
| Collodial silicon dioxide | 10.0 |
| Stearic acid | 5.0 |

The components are blended and compressed to form tablets, each weighing 240 mg.

EXAMPLE 4

Formulation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

EXAMPLE 5

Formulation 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

EXAMPLE 6

Formulation 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

EXAMPLE 7

Formulation 6

Suppositories, each containing 25 mg of active ingredient, are made as follows:

| Ingredient | Amount |
|---|---|
| Active Ingredient | 25 mg |
| Saturated fatty acids glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 8

Formulation 7

Suspensions, each containing 50 mg of medicament per 5.0 ml dose, are made as follows:

| Ingredient | Amount |
|---|---|
| Active Ingredient | 50.0 mg |
| Xanthan gum | 4.0 mg |
| Sodium carboxymethyl cellose (11%) | |
| Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 9

Formulation 8

Hard gelatin tablets, each containing 15 mg of active ingredient, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

EXAMPLE 10

Formulation 9

An intravenous formulation may be prepared as follows:

| Ingredient | (mg/capsule) |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

EXAMPLE 11

Formulation 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

EXAMPLE 12

Formulation 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:

1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/ Saline Stock Solution | q.s. ad 10.0 mL | q.s ad 100% |

Procedure:

1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix.

EXAMPLE 13

Determining Antiviral Activity of Compounds of the Invention

Work with Lassa fever virus presents significant logistical and safety issues due to the requirement for maximum laboratory containment (BSL-4). Therefore, surrogate assays for anti-Lassa fever virus activity were developed that would be suitable for evaluating large numbers of compounds under less-restrictive BSL-2 laboratory conditions. One such assay was developed to identify compounds that can block Lassa virus entry into the host cell. This assay uses only the envelope glycoprotein from Lassa fever virus, not the virus itself, and thus can safely be performed under normal BSL-2 conditions. The viral entry step is an attractive target for the development of antiviral pharmaceuticals, because it is an essential component of every viral life cycle. In addition, the antiviral targets, the interaction between the viral envelope and the host cell and subsequent structural rearrangement of the envelope, are specific to the virus. Thus, effective inhibitors are less likely to interfere with host processes.

Viral pseudotypes, which are generated by cotransfection of the Lassa envelope and a replication-defective HIV provirus with a luciferase reporter, are used to assess Lassa envelope function. The provirus is engineered so that the HIV envelope is not expressed, and thus heterologous viral envelope proteins are acquired as budding viral particles nonspecifically capture cell surface proteins. Pseudotypes prepared in this manner will infect cells via the heterologous envelope and are commonly used to assay functions of the heterologous envelope (2, 9, 26, 32, 34). Infection is measured by the luciferase signal produced from the integrated HIV reporter construct. The amount of infectious virus used to infect a cell culture line is directly proportional, over several orders of magnitude, to the luciferase-mediated luminescence produced in the infected cells. This assay was the basis of a high-throughput screen for Lassa virus entry inhibitors, against which a library of some 400,000 small molecule compounds was tested. Compounds that inhibited luciferase activity by at least 75% were subjected to a secondary specificity counter-screen, in which a second pseudotype using the unrelated Ebola virus glycoprotein was used as a specificity control. Compounds that inhibited both types of pseudotypes are likely either toxic to the cells or target the HIV platform, and were thus rejected. The remaining pool of compounds meeting these criteria (about 300-400) were further investigated for chemical tractability, potency, and selectivity.

Initially, the chemical structures of the hit compounds were examined for chemical tractability. A chemically tractable compound is defined as one that is synthetically accessible using reasonable chemical methodology, and which possesses chemically stable functionalities and potential drug-like qualities. Hits that passed this medicinal chemistry filter were evaluated for their potency. Compound potency was determined by evaluating inhibitory activity across a broad range of concentrations. Nonlinear regression was used to generate best-fit inhibition curves and to calculate the 50% effective concentration ($EC_{50}$). The selectivity or specificity of a given compound is typically expressed as a ratio of its cytotoxicity to its biological effect. A cell proliferation assay is used to calculate a 50% cytotoxicity concentration ($CC_{50}$); the ratio of this value to the $EC_{50}$ is referred to as the therapeutic index (T.I.=$CC_{50}/EC_{50}$). Two types of assays have been used to determine cytotoxicity, both of which are standard methods for quantitating the reductase activity produced in metabolically active cells (28). One is a calorimetric method that measures the reduction of 3-(4,5-dimethylthiazol-2-yl)-2,5-diphenyl-tetrazolium bromide (MTT), and the other uses fluorimetry to measure the reduction of resazurin (Alamar Blue). Selectivity could be further characterized by assessing the inhibitory action against viruses pseudotyped with unrelated viral envelopes. The $EC_{50}$ for hit compounds was determined for HIV pseudotypes bearing one of three different viral envelopes: Lassa, Ebola, and vesicular stomatitis virus (VSV). The ratio between $EC_{50}$s thus became a quantitative measure of compound specificity, and compounds with ratios less than 80 were rejected.

Twenty-five quality Lassa hits were discovered in the pool of initial hits from the pseudotype screening, all with $EC_{50}$ values below 1.8 μM. Ten of these compounds had $EC_{50}$s below 100 nM.

Compound ST-600037 was identified as one of the most potent and selective compounds from within the pool of 25 quality hits, in both the viral pseudotype assay and the Lassa fever virus plaque reduction assay (see Table 2 below). Chemical analogs of this compound were obtained from commercial vendors or were synthesized, and these analogs were tested as described in order to define the relationship between chemical structure and biological activity. Several of these analogs, in particular ST-600193, displayed enhanced potency and selectivity relative to ST-600037. In addition, ST-600193 is also a potent inhibitor of pseudotyped viral infection mediated by the envelopes of the New World arenaviruses Guanarito ($EC_{50}$<1 nM) and Tacaribe ($EC_{50}$=4 nM), demonstrating that this compound series may have utility for the treatment of *arenavirus* diseases other than Lassa fever.

TABLE 2

Antiviral Activity of Compounds of the Present Invention.

| No. | Activity against Lassa GP-pseudotyped-virus EC50 (μM) | specificity† | Activity vs. LFV* EC50 (μM) | T.I.** | formula | structure/name |
|---|---|---|---|---|---|---|
| 600037 | 0.016 | 900 | <0.1 | >400 | $C_{22}H_{21}N_3O_2$ | 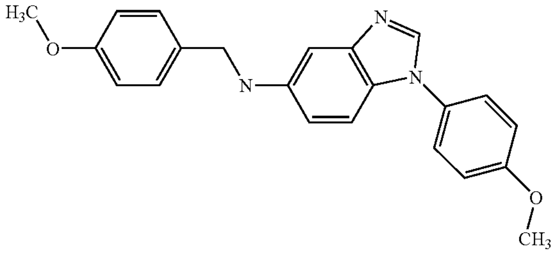 (4-methoxy-benzyl)-[1-(4-methoxy-phenyl)-1H-benzimidazol-5-yl]-amine |
| 600137 | >12 | unknown | n.d. | n.d. | $C_{23}H_{24}N_4O$ | 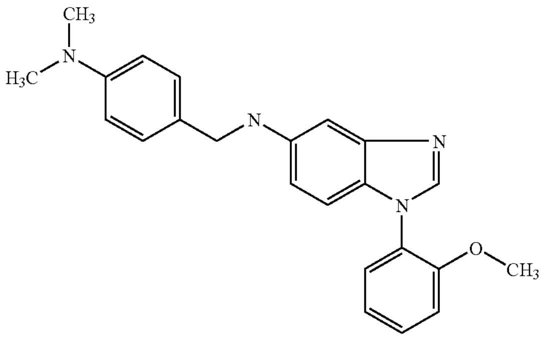 (4-dimethylamino-benzyl)-[1-(2-methoxy-phenyl)-1H-benzimidazol-5-yl]-amine |
| 600144 | 11 | >1 | n.d. | n.d. | $C_{22}H_{22}N_4$ | 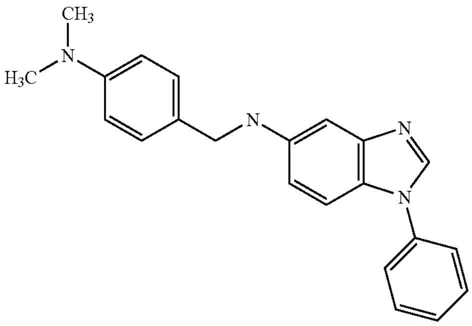 (4-dimethylamino-benzyl)-[1-phenyl-1H-benzimidazol-5-yl]-amine |

TABLE 2-continued

Antiviral Activity of Compounds of the Present Invention.

| No. | Activity against Lassa GP-pseudotyped-virus EC50 (μM) | specificity† | Activity vs. LFV* EC50 (μM) | T.I.** | formula | structure/name |
|---|---|---|---|---|---|---|
| 600145 | 0.04 | 300 | n.d. | n.d. | $C_{21}H_{18}N_3OBr$ | 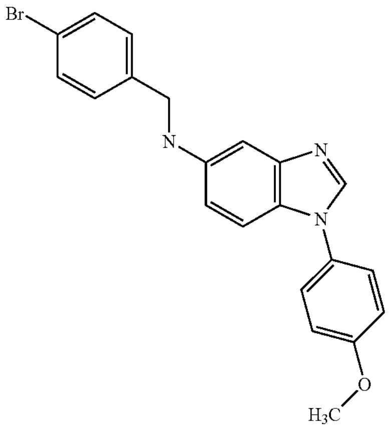 (4-bromo-benzyl)-[1-(4-methoxy-phenyl)-1H-benzimidazol-5-yl]-amine |
| 600146 | 0.3 | >40 | n.d. | n.d. | $C_{22}H_{21}N_3O_2$ | 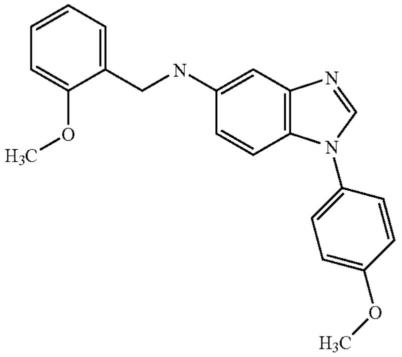 (2-methoxy-benzyl)-[1-(4-methoxy-phenyl)-1H-benzimidazol-5-yl]-amine |
| 600147 | 0.003 | >4000 | n.d. | n.d. | $C_{23}H_{23}N_3O_2$ | 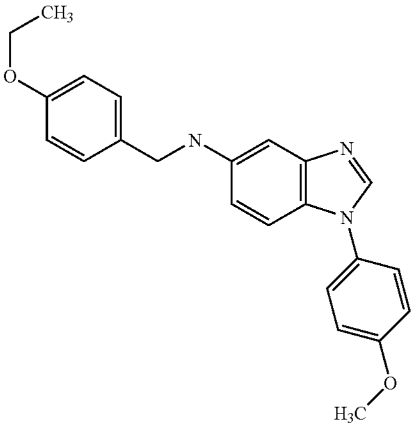 (4-ethoxy-benzyl)-[1-(4-methoxy-phenyl)-1H-benzimidazol-5-yl]-amine |

TABLE 2-continued

| Antiviral Activity of Compounds of the Present Invention. | | | | | | |
|---|---|---|---|---|---|---|
| | Activity against Lassa GP-pseudotyped-virus | | Activity vs. LFV* | | | |
| No. | $EC_{50}$ (μM) | specificity† | $EC_{50}$ (μM) | T.I.** | formula | structure/name |
| 600148 | 9 | none | n.d. | n.d. | $C_{22}H_{21}N_3O_2$ | 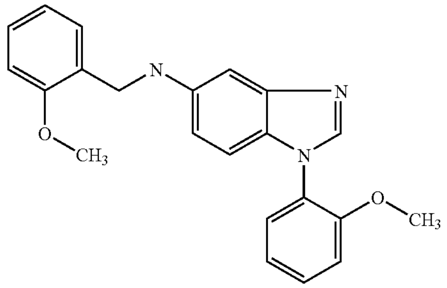 (2-methoxy-benzyl)-[1-(4-methoxy-phenyl)-1H-benzimidazol-5-yl]-amine |
| 600149 | 0.06 | >200 | n.d. | n.d. | $C_{25}H_{21}N_3O$ | 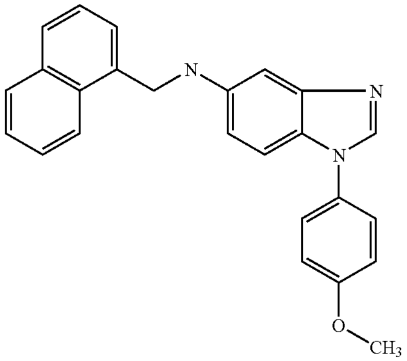 [1-(4-methoxy-phenyl)-1H-benzimidazol-5-yl]-napthalen-1-ylmethyl-amine |
| 600153 | 0.18 | >60 | n.d. | n.d. | $C_{21}H_{19}N_3O_2$ | 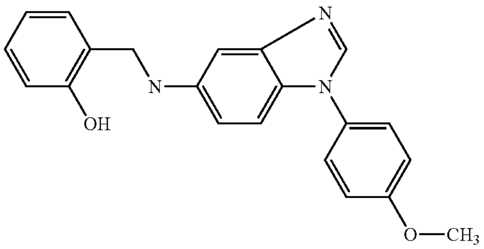 2-[[1-(4-methoxy-phenyl)-1H-benzimidazol-5-ylamino]-methyl]-phenol |

TABLE 2-continued

Antiviral Activity of Compounds of the Present Invention.

| No. | Activity against Lassa GP-pseudotyped-virus EC50 (μM) | specificity† | Activity vs. LFV* EC50 (μM) | T.I.** | formula | structure/name |
|---|---|---|---|---|---|---|
| 600169 | 0.02 | >500 | n.d. | n.d. | $C_{22}H_{21}N_3O$ | 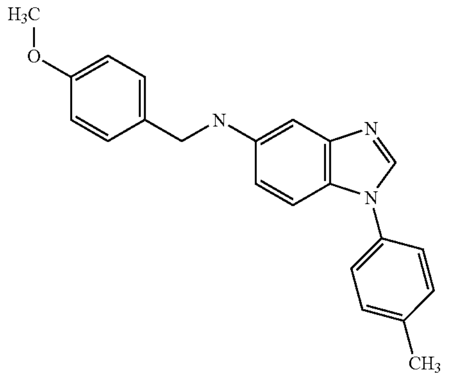 (4-methoxy-benzyl)-(1-p-tolyl-1H-benzimidazol-5-yl)-amine |
| 600170 | 0.04 | >200 | n.d. | n.d. | $C_{22}H_{18}N_3OCl$ | 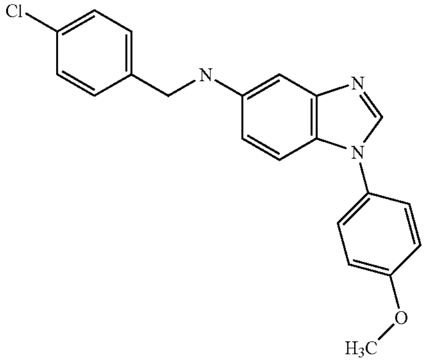 (4-chloro-benzyl)-[1-(4-methoxy-phenyl)-1H-benzimidazol-5-yl]-amine |
| 600172 | 0.7 | >10 | n.d. | n.d. | $C_{23}H_{23}N_3O_3$ | 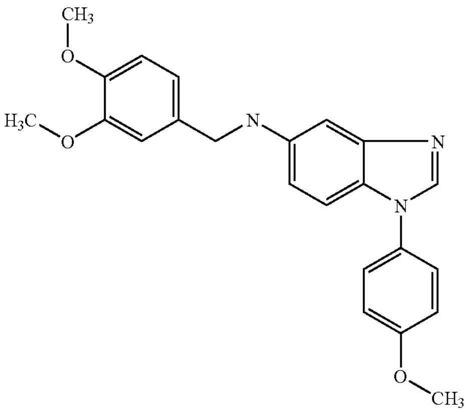 (3,4-dimethoxy-benzyl)-[1-(4-methoxy-phenyl)-1H-benzimidazol-5-yl]-amine |

TABLE 2-continued

Antiviral Activity of Compounds of the Present Invention.

| No. | Activity against Lassa GP-pseudotyped-virus EC50 (μM) | specificity† | Activity vs. LFV* EC50 (μM) | T.I.** | formula | structure/name |
|---|---|---|---|---|---|---|
| 600173 | 0.4 | >30 | n.d. | n.d. | $C_{20}H_{16}N_3Br$ | 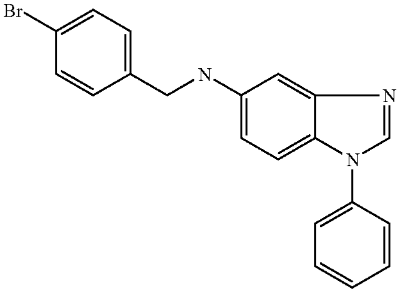 (4-bromo-benzyl)-(1-phenyl-1H-benzimidazol-5-yl)-amine |
| 600179 | 0.11 | >100 | n.d. | n.d. | $C_{30}H_{29}N_3O_4S$ | 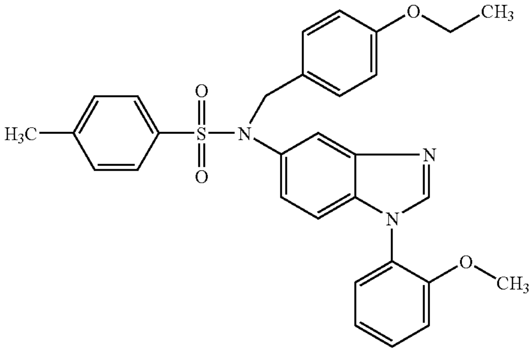 N-(4-ethoxy-benzyl)-N-[1-(2-methoxy-phenyl)-1H-benzimidazol-5-yl]-4-methylbenzenesulfonamide |
| 600188 | 0.003 | >4000 | n.d. | n.d. | $C_{22}H_{21}N_3O$ | 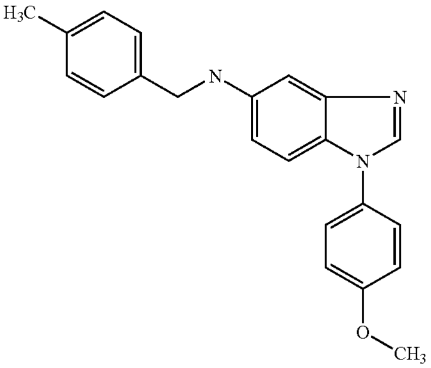 [1-(4-methoxy-phenyl)-1H-benzimidazol-5-yl]-(4-methyl-benzyl)-amine |

TABLE 2-continued

Antiviral Activity of Compounds of the Present Invention.

| | Activity against Lassa GP-pseudotyped-virus | | Activity vs. LFV* | | | |
|---|---|---|---|---|---|---|
| No. | $EC_{50}$ (μM) | specificity† | $EC_{50}$ (μM) | T.I.** | formula | structure/name |
| 600189 | 0.1 | 100 | n.d. | n.d. | $C_{23}H_{23}N_3O_3$ | 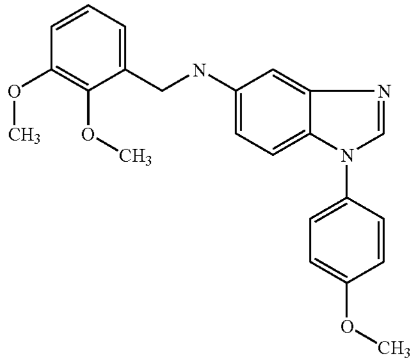 (2,3-dimethoxy-benzyl)-[1-(4-methoxy-phenyl)-1H-benzimidazol-5-yl]-amine |
| 600190 | 2 | 3 | n.d. | n.d. | $C_{22}H_{21}N_3O_2$ | 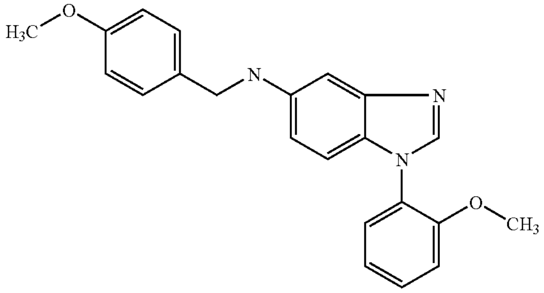 (4-methoxy-benzyl)-[1-(2-methoxy-phenyl)-1H-benzimidazol-5-yl]-amine |
| 600191 | 0.04 | >300 | n.d. | n.d. | $C_{22}H_{21}N_3O_2$ | 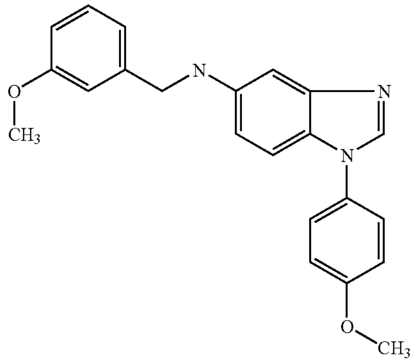 (3-methoxy-benzyl)-[1-(4-methoxy-phenyl)-1H-benzimidazol-5-yl]-amine |

TABLE 2-continued

Antiviral Activity of Compounds of the Present Invention.

| No. | Activity against Lassa GP-pseudotyped-virus EC50 (μM) | specificity† | Activity vs. LFV* EC50 (μM) | T.I.** | formula | structure/name |
|---|---|---|---|---|---|---|
| 600192 | 5 | none | n.d. | n.d. | $C_{23}H_{23}N_3O_3$ | 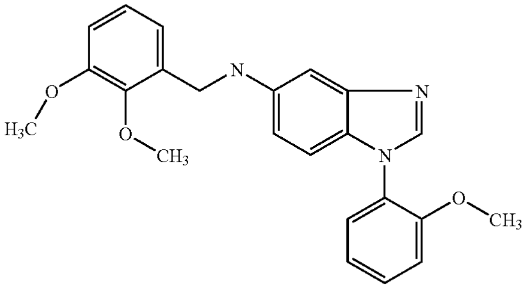 (2,3-dimethoxy-benzyl)-[1-(2-methoxy-phenyl)-1H-benzimidazol-5-yl]-amine |
| 600193 | 0.0011 | 13,000 | <0.1 | >400 | $C_{24}H_{25}N_3O$ | 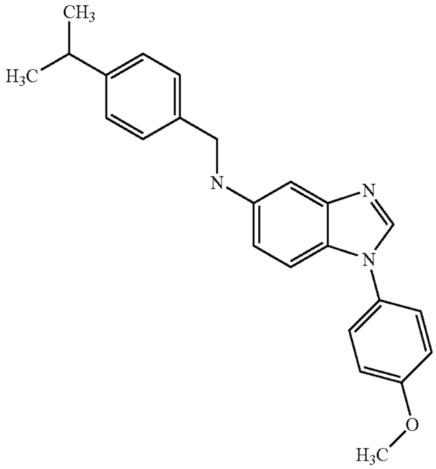 (4-isopropyl-benzyl)-[1-(4-methoxy-phenyl)-1H-benzimidazol-5-yl]-amine |
| 600196 | 0.03 | >400 | n.d. | n.d. | $C_{21}H_{19}N_3O$ | 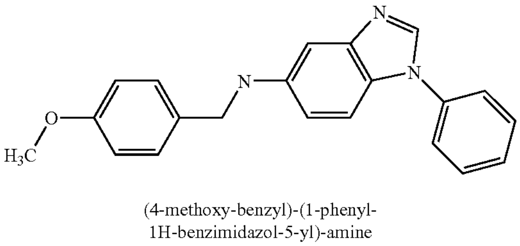 (4-methoxy-benzyl)-(1-phenyl-1H-benzimidazol-5-yl)-amine |
| 600362 | 0.4 | 40 | n.d. | n.d. | $C_{26}H_{27}N_3O_2$ | 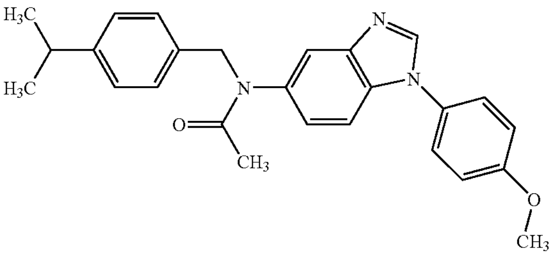 |

TABLE 2-continued

Antiviral Activity of Compounds of the Present Invention.

| No. | Activity against Lassa GP-pseudotyped-virus EC$_{50}$ (μM) | specificity[†] | Activity vs. LFV* EC$_{50}$ (μM) | T.I.** | formula | structure/name |
|---|---|---|---|---|---|---|
| | | | | | | N-(4-isopropyl-benzyl)-N-[1-4-methoxy-phenyl)-1H-benzimidazol-5-yl]-acetamide |
| 600363 | 0.2 | 100 | n.d | n.d | $C_{31}H_{31}N_3O_3S$ | 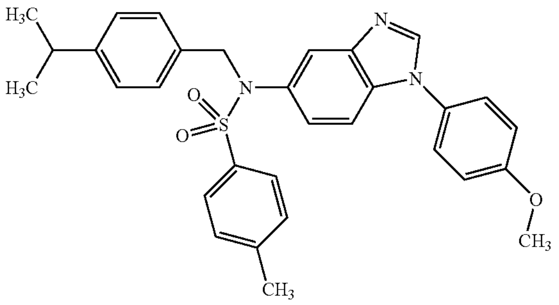 N-(4-isopropyl-benzyl)-N-[1-(4-methoxy-phenyl)-1H-benzimidazol-5-yl]-4-methylbenzenesulfonamide |

*Lassa fever virus plaque reduction (Josiah strain) performed under BSL-4 conditions

[†]EC$_{50}$ ratio calculated as (EC$_{50}$ for negative control [VSV or Ebola, whichever was lower])/(EC$_{50}$ for Lassa)

**T.I. (therapeutic index) is the ratio of cytotoxicity to effective anti-Lassa concentrations (CC$_{50}$/EC$_{50}$) on Vero cells

EXAMPLE 14

Determining Antiviral Activity of Compounds of the Invention

As discussed in Example 13 above, anti-infective drug discovery for LASV presents significant logistical and safety challenges due to the requirement for maximum laboratory containment (BSL-4). Therefore, a surrogate assay, in which the LASV envelope glycoprotein (GP) was incorporated into retroviral pseudotypes, was used as a high-throughput screening (HTS) platform. *Arenavirus* entry is mediated by this single virally-encoded protein, categorized as a class I viral fusion protein (Gallaher W R (2001) *BMC Microbiol* 1:1; York J (2005) *Virology* 343:267-274; Eschli B (2006) *J Virol* 80-5897-5907), facilitating the effective use of pseudotypes for antiviral screening. Inhibitors of LASV GP-mediated viral entry could thus be identified from a library of small molecule compounds. As an essential component of the viral life cycle, the entry process is an attractive target for the development of antiviral pharmaceuticals. For example, two distinct classes of viral entry inhibitor, enfuvirtide (Matthews T, et al. (2004) *Nat Rev Drug Discov* 3:215-225) and maraviroc (Dorr P, et al. (2005) *Antimicrob Agents Chemother* 49:4721-4732), have recently been approved for H IV treatment.

Materials and Methods

Virus, Cells, and Compounds. Viruses and Vero cells were described previously (Bolken T C, et al. (2006) *Antiviral Res* 69:86-97). 293T/17 cells (ATCC CRL-11268) were maintained in Dulbecco's modified Eagle medium (DMEM) with 10% heat-inactivated fetal bovine serum (FBS) (Invitrogen) at 37° C. with 5% $CO_2$. Initial compound lots were purchased from commercial suppliers (ST-37 from Asinex and ST-193 from InterBioScreen), while subsequent batches have been custom synthesized by a number of different vendors. Compound stock solutions were made at 10 mM in dimethyl sulfoxide (DMSO).

Viral Glycoprotein Cloning. Viral RNA isolated with a QIAamp Viral RNA kit (Qiagen) served as a template for cDNA synthesis using SuperScript One-Step RT-PCR (Invitrogen) and GP-specific primers. GP inserts, except for JUNV GP (see below), were subsequently subcloned into the mammalian expression vector pCAGGS (Niwa H, et al. (1991) *Gene* 108:193-199). Junin GP cDNA was subcloned into pCI (Promega) via PCR with engineered, flanking Kpn I-Bam HI restriction sites. GenBank accession numbers are provided in the FIG. 4 legend, with the following deviations relative to the deposited sequences (all numbering relative to the relevant GP ORF): MACV GP had one synonymous nucleotide (nt) substitution ($T_{552}C$); JUNV GP had one synonymous nt substitution ($C_{1446}T$); PICV GP had one coding substitution ($G_{395}A$ nt change coding for a $S_{132}N$ a.a. change); and TCRV GP differed from a previously reported sequence (Allison LMC, et al. (1991) *J Gen Virol* 72:2025-2029) at three locations: $C_{297}T$ (synonymous substitution) and GA to AG at nt 1336-7, coding for a $E_{446}R$ a.a. change. The LASV-LCMV chimeras were created by overlapping PCR, fusing the 5' 1245 (LASV) or 1263 nt (LCMV) with the 3' 231 (LASV) or 234 nt (LCMV) of the GP ORF (numbering includes termination codon); the protein fusion junction is thus C-terminal of a common TEML (single a.a. code) sequence. *Arenavirus* GP point mutations were introduced with the QuikChange Site-Directed Mutagenesis kit (Stratagene). LASV $V_{431}M$ (LASV #1 in Table 4) was generated by substitution of 2 nt ($G_{1291}A$, $T_{1293}G$) within codon 431, LASV $V_{435}M$ (LASV #2 in Table 4) was a single nt substitution ($G_{1303}A$), and LASV dbl contained both a.a. changes. LCMV $M_{437}V$ (LCMV #1 in Table 4) was generated by a $A_{1309}G$ nt substitution, and LCMV dbl ($M_{437}V$, $M_{441}V$) also contained a $A_{1321}G$ nt change. Pichinde $T_{445}V$ (Pichinde #1 in Table 4) was made by substituting GT for AC at nt 1333-4.

Generation of ST-193-resistant TCRV variants. Vero cells were initially infected with TCRV at an MOI of 0.1 in minimal essential media (MEM) with 2% FBS in the presence of 1.2 μM ST-193. Virus was harvested when cytopathic effect became apparent (~7-10 days) and passaged again at a higher ST-193 concentration (1.8 μM); this process was repeated at 2.4 and 3 μM ST-193. RNA was isolated from the last virus harvest and cDNA prepared as above, followed by cloning into TOPO TA vector pCR2.1 (Invitrogen). Multiple clones were then sequenced and subcloned into pCAGGS using Eco RI-Xho I restriction sites.

Pseudotyped virus production. Pseudovirions were generated with a three-plasmid, HIV-based expression system (Naldini L, et al. (1996) Science 272-263-267). 293T/17 cells were transfected (CalPhos Mammalian Transfection kit, BD Biosciences) with a 1:1:1.7 ratio of pΔR8.2, pHR'-Luc, and GP expression construct (1:1:0.6 for VSVg) and induced with 10 mM sodium butyrate for 6 hours, 20-26 hours post-transfection (applied only to non-VSVg envelopes). Supernatants were harvested 48 hours post-transfection, clarified by low-speed centrifugation (100×g for 4 min.), filtered with a 0.45 μM syringe filter, and stored in aliquots at −80° C.

Infections and inhibition assays. 293T/17 cells seeded in poly-D-lysine-coated 96-well plates were infected with pseudovirions in DMEM+7.5% FBS+0.5% DMSO and assayed for firefly luciferase activity (Luciferase Assay System from Promega) at 72 hours post-infection. Luminescense was quantitated on a Wallac EnVision 2102 Multilabel plate reader (PerkinElmer) using 1 second read time per well. Luciferase signal was directly proportional to inoculum size over several orders of magnitude. In order to test for antiviral activity, serial compound dilutions in DMSO were added in triplicate to cells immediately prior to virus addition, maintaining 0.5% final DMSO concentration in all wells. Each 96-well plate had a minimum of four replicates of a negative control (no virus) and eight replicates of a positive control (virus without compound). Test well luciferase activity was converted to % of the positive control, and $IC_{50}$s were calculated using XLfit (IDBS) for Microsoft Excel with a one site dose-response curve fit.

Figure 1B:
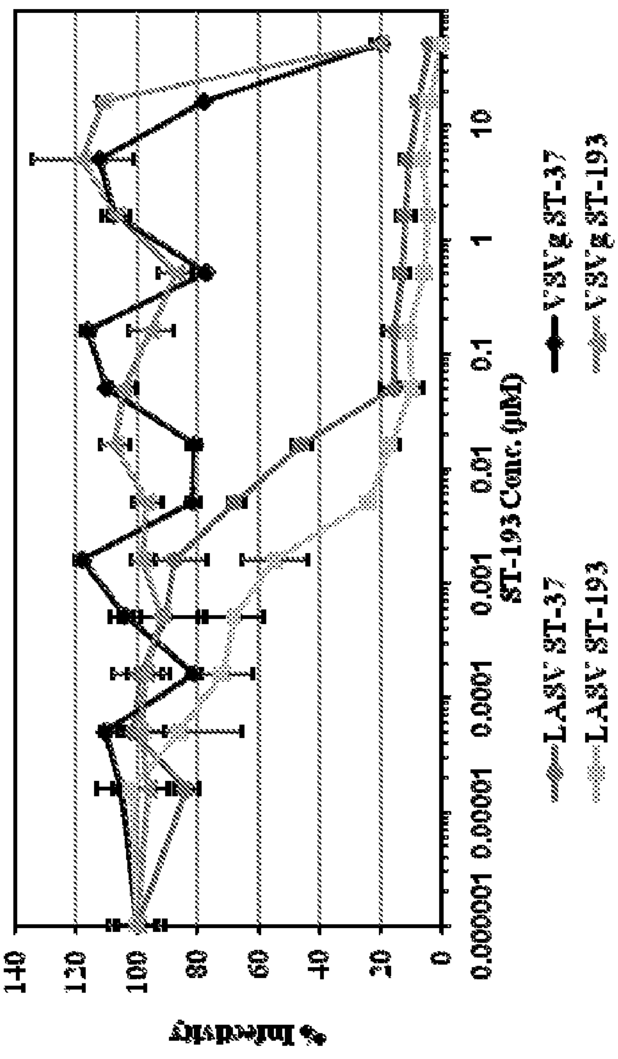

Identification and activity of ST-193. A chemically diverse library of about 400,000 small molecules was screened with retroviral-based pseudotypes incorporating the LASV GP. Hit compounds were filtered through a battery of follow-up tests, including specificity assays, cytotoxicity assays, confirmation assays against authentic Lassa fever virus, and validation of antiviral activity with re-synthesized compound. ST-37, a benzimidazole derivative exhibiting an average $IC_{50}$ against LASV GP pseudotypes of 16 nM (FIG. 1A), was identified from this process. In order to characterize the relationship between chemical structure and biological activity (structure-activity relationship, or SAR), analogs of ST-37 were assayed for antiviral activity. One of these analogs, ST-193 (FIG. 1A; (4-isopropyl-benzyl)-[1-(4-methoxy-phenyl)-1H-benzimidazol-5-yl]-amine), substitutes an isopropyl for a methoxy group, resulting in significantly greater antiviral potency (FIG. 1B). A non-*arenavirus* envelope, the G protein from vesicular stomatitis virus (VSVg), is used as a specificity control. As a practical consideration, compounds are tested at concentrations no higher than 50 μM, a level at which ST-193 exhibits visual evidence of insolubility (crystals observed by light microscopy); this is also near the 50% cytotoxicity concentration (ST-193 $CC_{50}$=48 μM on 293T/17 cells), and thus the VSVg inhibition seen at the highest concentration is considered to be nonspecific activity ($IC_{50}$ around 30 μM; FIG. 1B).

The activity and specificity of ST-193 has been assessed by a variety of assays, including pseudotype infectivity, virus yield reduction, plaque reduction, and cytopathic effect. The pseudotype platform was the most reproducible and amenable to direct comparison between diverse viruses, particularly given that several viruses of interest are restricted to use under BSL-4 containment. As shown in Table 3, ST-193 potently inhibits envelopes derived from clade B New World arenaviruses, the phylogenetic cluster containing all four South American hemorrhagic fever viruses (Junin, Machupo, Guanarito, and Sabia). ST-193 also potently inhibits viral entry mediated by the GP from the prototypic New World *arenavirus*, Tacaribe virus (TCRV). TCRV, another clade B member, is not known to be a significant human pathogen. Surprisingly, ST-193 exhibits only a nonspecific level of activity against the LASV-related LCMV GP, with an $IC_{50}$ some four orders of magnitude greater than against LASV (Table 3).

TABLE 3

ST-193 antiviral activity against retroviral-based pseudotypes incorporating heterologous envelope glycoproteins.

| GP | Phylogeny of GP source | $IC_{50}$ (μM) ± SEM |
|---|---|---|
| Lassa | Old World arenavirus; Josiah strain | 0.0016 ± 0.0003 |
| LCMV | Old World arenavirus; Armstrong 53b | 31 ± 4 |
| Pichinde | New World arenavirus, clade A | 2.6 ± 0.5 |
| Junín | New World arenavirus, clade B1 | 0.0002 ± 0.00003 |
| Machupo | New World arenavirus, clade B1 | 0.0023 ± 0.0013 |
| Tacaribe | New World arenavirus, clade B1 | 0.004 ± 0.002 |
| Guanarito | New World arenavirus, clade B2 | 0.00034 ± 0.00007 |
| Sabia | New World arenavirus, clade B3 | 0.012 ± 0.003 |
| VSV | rhabdovirus | 29 ± 2.5 |

Mapping determinants of ST-193 sensitivity. To gain insight into the mechanism of ST-193 inhibition and potential binding sites, three strategies were employed to identify determinants of ST-193 sensitivity within the *arenavirus* envelope glycoprotein. First, domain swapping experiments were performed using two closely-related *arenavirus* GPs, one sensitive (LASV) and one insensitive (LCMV) to ST-193. Second, a nonpathogenic surrogate virus (TCRV) was passaged in the presence of ST-193 to select for less-sensitive variants. Finally, site-directed mutagenesis identified two significant amino acids located within the predicted transmembrane domain (TMD) of the GP2 subunit.

Figure 2A:
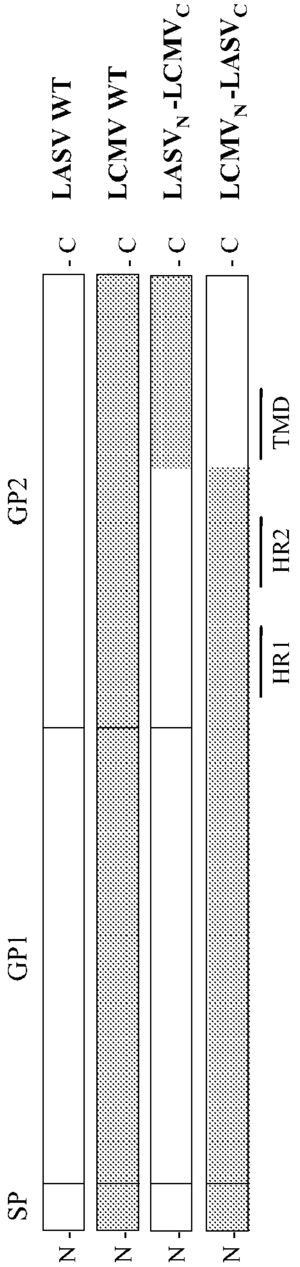
FIGS. 2A and 2B show domain swapping which demonstrates that the C-terminal third of GP2 determines sensitivity to ST-193. (2A) Schematic representation of LASV-LCMV chimeric GPs. Predicted TMD and heptad repeat domains (HR1 and HR2) are indicated. The two GPs are spliced 12 a.a. N-terminal of the predicted TMD. (2B) Pseudotype infectivity as in FIG. 1 using the *arenavirus* GPs shown (representative experiment). Average $IC_{50}$s±SEM for these constructs (across at least four experiments) were: LASV, 0.0016±0.0003 μM; LCMV, 31±4 μM; $LASV_N$-$LCMV_C$, 13.6±2.2 μM; and $LCMV_N$-$LASV_C$, 0.0005±0.0003 μM.
Figure 2B:
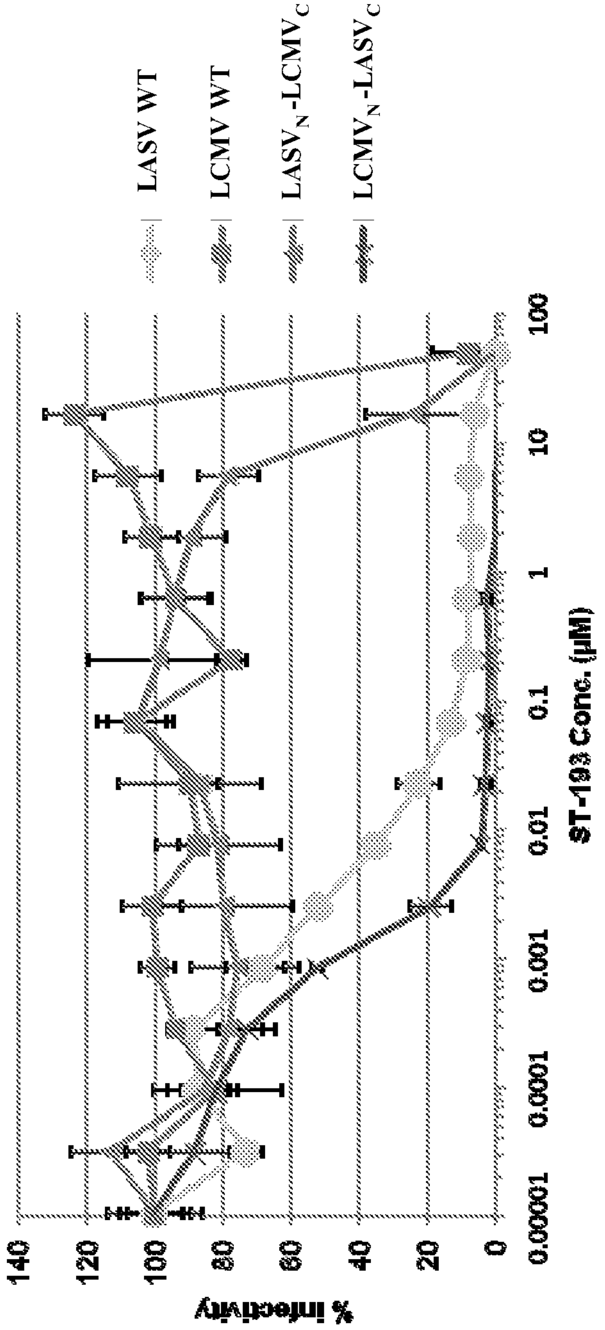

C-terminal portion of the LASV GP2 subunit confers ST-193 sensitivity. Retroviral pseudotypes incorporating chimeric *arenavirus* envelopes were constructed to identify the region dictating ST-193 sensitivity. Constructs that exchanged the C-terminal one-third of the GP2 subunit (76 a.a. of LASV, 77 a.a. of LCMV) were found to retain viral entry function. These chimeras partition the entire endodomain and predicted TMD from the signal peptide, the GP1 subunit, and most of the GP2 subunit ectodomain (FIG. 2A), including the N-terminal and most of the C-terminal heptad repeats characteristic of class I viral fusion proteins (Gallaher W R, et al. (2001) *BMC Microbiol* 1:1.16-18; York J, et al. (2005) *Virology* 343:267-274; and Eschli B, et al. (2006) *J Virol* 80:5897-5907). ST-193 sensitivity was found to be conferred by the C-terminal portion of GP2 (FIG. 2B).

Generation and characterization of ST-193-resistant TCRV variants. In order to genetically map sensitivity determinants, TCRV was serially passaged in the presence of escalating concentrations of ST-193 to select for variants with decreased sensitivity. A selected population (193R) was thus generated that yielded equivalent viral titers when cultured in the presence or absence of 3 μM ST-193; in contrast, unselected TCRV titer is reduced 1000-fold under corresponding conditions (data not shown). RNA from the selected population was used to synthesize cDNA, and multiple GP sequences were determined from clones derived from this cDNA. Coding changes found within any GP sequence were subsequently introduced into a TCRV GP expression plasmid for viral pseudotype production in order to directly evaluate the contribution of a given mutation to ST-193 sensitivity. Although this approach gives little consideration to viral fitness, it allows for simple and rapid identification of multiple sensitivity determinants.

Figures 3A, 3B:
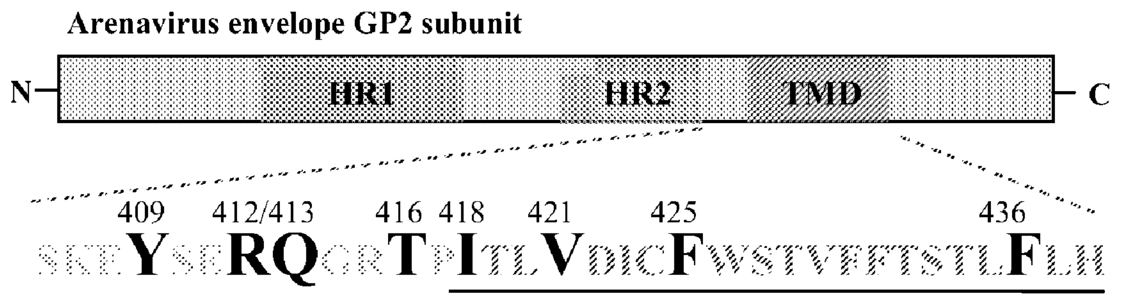
FIGS. 3A and 3B show ST-193 sensitivity determinants. (3A) Schematic representation of an *arenavirus* GP2 subunit and the sites of 193R variations. The TCRV amino acid sequence is shown for the region indicated, with sites identified as determinants of ST-193 sensitivity indicated with raised letters and numbering (TCRV GP amino acid numbering). Predicted TMD and heptad repeat domains (HR1 and HR2) are indicated (TMD is outlined in the sequence). (3B) Single amino acid variations that reduce ST-193 sensitivity in TCRV GP. Resistance is the fold change in $IC_{50}$ as measured with TCRV GP-pseudotyped HIV, relative to wild-type, and averaged across at least four independent experiments (each in triplicate).

Individual 193R mutations that reduce ST-193 sensitivity were found in or immediately N-terminal of the predicted TMD of the GP2 subunit (FIG. 3). The 193R variations resulted in a range of resistance as single amino acid changes increased the ST-193 $IC_{50}$ by 30-fold to more than 1000-fold. At position 413, located within the predicted ectodomain near the TMD, two distinct mutations ($Q_{413}H$ and $Q_{413}R$) resulted in greatly reduced ST-193 sensitivity.

Interestingly, resistance to a previously-described inhibitor of New World *arenavirus* entry, ST-294, has been mapped to a similar location within the TCRV GP2 subunit (Bolken T C, et al. (2006) *Antiviral Res* 69:86-97). Three of the four recognized ST-294-resistant TCRV variants (DR1-4) also exhibited reduced sensitivity to ST-193 (FIG. 3), while the fourth (DR3, or $S_{433}I$) retained full sensitivity. The ST-294 DR4 mutation ($F_{436}I$) was also identified from within the 193R population. Conversely, the other 193R variants retain ST-294 sensitivity (data not shown). A mutation identified from a third distinct TCRV selection, $R_{412}T$, was also found to display ST-193 resistance (FIG. 3). This third screen was designed to identify resistance to ST-761, another New World *arenavirus* inhibitor that targets the GP protein. As with the ST-294 comparison, 193R variants retain sensitivity to ST-761, with the exception of the $F_{436}I$ variant. ST-193, ST-294, and ST-761 are chemically diverse small molecules with no obvious common characteristic.

Figure 4:
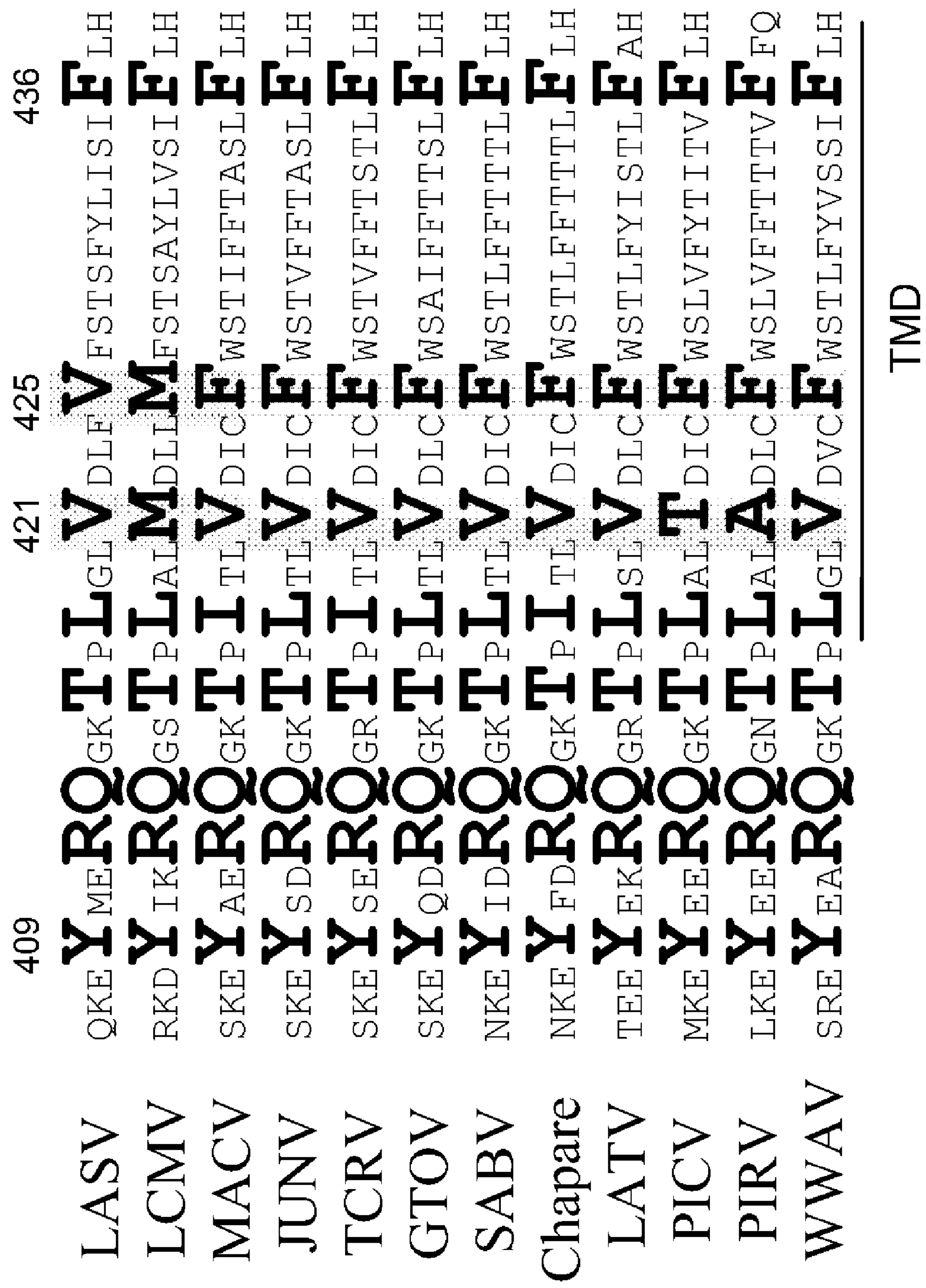
FIG. 4 shows amino acid alignment of a portion of the *arenavirus* GP2 subunit. Amino acid numbering as in FIG. 3. Residues identified as ST-193 sensitivity determinants (FIG. 3) are in bold type, and the predicted TMD is indicated. The highlighted residues at positions 421 and 425 are sensitivity determinants for which some sequence divergence is observed across the Arenaviridae family. Abbreviations and GenBank accession numbers are as follows: LASV, Lassa fever strain Josiah (J04324); LCMV, lymphocytic choriomeningitis strain Armstrong 53b (AY847350); MACV, Machupo strain Carvallo (AY619643); JUNV, Junin strain MC2 (D10072); TCRV, Tacaribe strain TRVL 11598 (P31840); GTOV, Guanarito (NC_005077); SABV, Sabia (NC_006317); LATV, Latino strain Maru 10924 (AF485259); PICV, Pichinde (U77602); PIRV, Pirital (NC_005894); and WWAV, Whitewater Arroyo (AF228063). LASV and LCMV are classified as Old World arenaviruses, while New World arenaviruses are represented by PICV and PIRV (clade A); MACV, JUNV, TCRV, GTOV, and SABV (clade B); and LATV (clade C). WWAV is likely a recombinant of clades A and B.

Two TMD residues regulate ST-193 sensitivity. Alignment of *arenavirus* GP protein sequences reveals conservation of the majority of ST-193 sensitivity determinants identified above (FIG. 4). Positions 421 and 425 show some diversity, however, which could in part explain the relative insensitivity of LCMV and Pichinde virus GPs to ST-193. Position 421 in particular is striking in that *arenavirus* GPs sensitive to ST-193 in the nanomolar range contain valine, while those that are not contain other residues (methionine or threonine). To directly test the functional significance of residue 421 with respect to ST-193 sensitivity, the LASV GP was engineered to contain the corresponding amino acid from ST-193-insensitive LCMV at one or both of these sites (Table 4). Additionally, some of the reciprocal changes were made in the LCMV GP, and the $Val_{421}$ present in ST-193-sensitive GPs was introduced into the Pichinde GP. Viral pseudotypes were made to evaluate ST-193 sensitivity for each of these genotypes.

TABLE 4

Site-directed mutagenesis of predicted ST-193 sensitivity determinants.

| GP | Site #1 (421)* | Site #2 (425)* | $IC_{50}$ (μM) ± SEM | $IC_{50}$ relative to LASV |
|---|---|---|---|---|
| LASV wt | Val | Val | 0.0016 ± 0.0003 | - 1 - |
| LASV dbl | Met | Met | 24 ± 3 | 15,200 |
| LASV #1 | Met | Val | 1.4 ± 0.3 | 850 |
| LASV #2 | Val | Met | 6.1 ± 1.3 | 3800 |
| LCMV wt | Met | Met | 31 ± 4 | 19,600 |
| LCMV #1 | Val | Met | 27 ± 4 | 16,900 |
| LCMV dbl | Val | Val | 26 ± 4 | 16,200 |
| Pichinde wt | Thr | Phe | 2.6 ± 0.5 | 1600 |
| Pichinde #1 | Val | Phe | 0.046 ± 0.025 | 29 |

*TCRV GP numbering of aligned arenavirus GP sequences

Introduction of a methionine into either position 421 or 425 dramatically reduces the sensitivity of LASV to ST-193, and substitution of both residues further reduces the sensitivity such that LASV dbl GP ($V_{421}M$, $V_{425}M$) and LCMV GP display nearly equivalent ST-193 sensitivity (Table 4). The reciprocal substitutions (LCMV dbl and LCMV #1), however, do not convert LCMV GP to greater sensitivity, indicating that other residues play a role in LCMV resistance to ST-193 inhibition. The significance of position 421 is further highlighted by the increased ST-193 sensitivity of Pichinde GP when valine is exchanged for the native threonine residue (Table 4).

The benzimidazole derivative described here, ST-193, has been demonstrated to be a potent inhibitor of *arenavirus* entry. Without being bound by theory, the present evidence suggest that ST-193 does not directly block virus attachment. First, domain swapping experiments demonstrate that the difference in sensitivity between LASV and LCMV resides not within the receptor-binding GP1 domain, but in the GP2 domain. Second, no sensitivity determinants were identified within GP1 following selection for ST-193-resistant *arenavirus*. Finally, *arenavirus* entry is mediated by a diversity of host cell surface receptors that do not appear to correspond to ST-193 sensitivity. LASV and LCMV utilize α-dystroglycan (Cao W, et al. (1998) *Science* 282:2079-2081), while the Category A hemorrhagic New World arenaviruses use transferrin receptor 1 (Radoshitzky S R, et al. (2007) *Nature* 446:92-96). Clade C New World arenaviruses, like the Old World arenaviruses, use α-dystroglycan (Spiropoulou C F, et al. (2002) *J Virol* 76:5140-5146). Some other New World arenaviruses, including ST-193-sensitive TCRV, likely use a distinct, yet-unidentified receptor (Flanagan M L, et al. (2008) *J Virol* 82:938-948; Oldenburg J, et al. (2007) *Virology* 364:132-139; Reignier T, et al. (2008) *Virology* 371:439-446; and Rojek J M, et al. (2006) *Virology* 349:476-491). These observations, combined with the presence of multiple ST-193 sensitivity determinants within the fusogenic GP2 subunit, suggest that ST-193 blocks GP-mediated entry at a post-attachment stage.

ST-193 sensitivity is modulated by a 28 amino acid span of the GP2 subunit of the envelope protein, encompassing nearly the entire predicted TMD. Although these results implicate this region in ST-193 activity, the location and spacing of the identified sensitivity determinants suggest that at least some of these sites may not be directly involved in inhibitor binding. Notably, the two residues implicated in the phylogeny of ST-193 sensitivity, positions 421 and 425, are located four amino acids apart. Within an α-helical TMD, these two residues are likely adjacent to one another; position 418, another important sensitivity determinant (FIG. 2B), lies on the same helical face as well. The predicted physical property of ST-193 (average calculated partition coefficient, or cLogP, of 5.5) is consistent with binding a hydrophobic pocket. ST-193 might prevent or perturb conformational rearrangement of GP, or inhibit lipid mixing, thereby preventing fusion with the host cell. Alternatively, ST-193 could interact with the membrane-proximal domain, in the 409-413 region identified following genetic selection; although this region is more hydrophilic, the membrane-proximal ectodomain of HIV gp41 (the class I viral fusion protein equivalent of *arenavirus* GP2) is a target of broadly-neutralizing monoclonal antibodies (Sun Z-Y J, et al. (2008 *Immunity* 28:52-63). Another possibility is that ST-193 might disrupt protein-protein interactions within or near the TMD. Interactions between the TMDs of alphavirus E1 and E2 proteins are important for fusion (Sjöberg M, et al. (2003) *J Virol* 77:3441-3450). Several recent studies have investigated the unusual role of the *arenavirus* GP signal peptide (Agnihothram S S, et al. (2006) *J Virol* 80:5189-5198; Agnihothram S S, et al. (2007) *J Virol* 81:4331-4337; Eichler R, et al. (2003) EMBO Rep 4:1084-1088; Eichler R, et al. (2004) *J Biol Chem* 279:12293-12299; Froeschke M, et al. (2003) *J Biol Chem* 278:41914-41920; Kunz S, et al. (2003) *Virology* 314:168-178; Saunders A A, et al. (2007) *J Virol* 81:5649-5657; Schrempf S, et al. (2007) *J Virol* 81: 12515-12524; York J, et al. (2006) *J Virol* 80:7775-7780; York J, et al. (2007) *J Virol* 81:13385-13391; York J, et al. (2004) *J Virol* 78:10783-10792), which remains associated with GP and is required for efficient GP1-GP2 processing, transport to the plasma membrane, membrane fusion, and virus infectivity. This cleaved, 58 amino acid peptide has two conserved hydrophobic domains and a hydrophilic amino terminus. The interaction between the stable signal peptide and the processed GP1-GP2 complex, then, might provide a vulnerable antiviral target specific to arenaviruses. Sensitivity to at least three dissimilar antiviral compounds (ST-193, ST-294, and ST-761) has been mapped to the TMD region of GP2, with overlapping yet quite distinct patterns of genetic resistance. By way of analogy, several different classes of small molecule HIV entry inhibitor, including maraviroc, are thought to bind within a pocket created by four TMDs of CCR5, an important HIV co-receptor (Kondru R (2008) *Mol Pharmacol* 73:789-800).

Arenaviruses constitute an important class of hemorrhagic fever pathogen, with five viruses designated Category A. The potency and spectrum of ST-193 activity make it a strong antiviral compound for the prevention and treatment of disease caused by these viruses.

All references cited herein are herein incorporated by reference in their entirety for all purposes.

We claim:

1. A method for the treatment of an *Arenavirus* viral infection, comprising administering in a therapeutically effective amount to a mammal in need thereof, a compound of Formula I below:

I

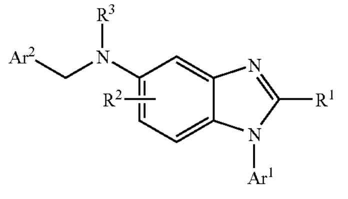

wherein $R^1$ and $R^2$ are independently hydrogen, alkyl, alkenyl, alkynyl, cycloalkyl, arylalkyl, aryl, acyl, arylacyl, hydroxy, alkyloxy, alkylthio, amino, alkylamino, acetamido, halogen, cyano or nitro;

$R^3$ is hydrogen, acyl, arylacyl or sulfonyl; and $Ar^1$ and $Ar^2$ are independently substituted or unsubstituted aryl, wherein said *Arenavirus* is selected from the group consisting of Lassa, Junin, Machupo, Guanarito, Sabia, Whitewater Arroyo, Chapare, LCMV and LCMV-like viruses.

2. The method of claim 1, wherein $R^1$ is hydrogen.

3. The method of claim 1, wherein $R^2$ is hydrogen.

4. The method of claim 1, wherein $R^3$ is hydrogen.

5. The method of claim 1, wherein $R^3$ is $-S(O)_2$-substituted aryl.

6. The method of claim 5, wherein $R^3$ is $-S(O)_2$-substituted phenyl.

7. The method of claim 6, wherein $R^3$ is $-S(O)_2$-alkoxyphenyl.

8. The method of claim 7, wherein $R^3$ is $-S(O)_2$-methoxyphenyl.

9. The method of claim 7, wherein $R^3$ is $-S(O)_2$-p-methoxyphenyl.

10. The method of claim 1, wherein $Ar^1$ is unsubstituted aryl.

11. The method of claim 10, wherein $Ar^1$ is unsubstituted phenyl.

12. The method of claim 1, wherein $Ar^1$ is mono-substituted aryl.

13. The method of claim 12, wherein $Ar^1$ is mono-substituted phenyl.

14. The method of claim 13, wherein $Ar^1$ is alkoxyphenyl.

15. The method of claim 14, wherein $Ar^1$ is methoxyphenyl.

16. The method of claim 15, wherein $Ar^1$ is o-methoxyphenyl.

17. The method of claim 15, wherein $Ar^1$ is p-methoxyphenyl.

18. The method of claim 1, wherein $Ar^2$ is substituted aryl.

19. The method of claim 18, wherein $Ar^2$ is substituted phenyl.

20. The method of claim 19, wherein $Ar^2$ is mono-substituted phenyl.

21. The method of claim 20, wherein $Ar^2$ is alkoxyphenyl.

22. The method of claim 21, wherein $Ar^2$ is methoxyphenyl.

23. The method of claim 22, wherein $Ar^2$ is o-methoxyphenyl.

24. The method of claim 22, wherein $Ar^2$ is m-methoxyphenyl.

25. The method of claim 22, wherein $Ar^2$ is p-methoxyphenyl.

26. The method of claim 21, wherein $Ar^2$ is ethoxyphenyl.

27. The method of claim 26, wherein $Ar^2$ is p-ethoxyphenyl.

28. The method of claim 20, wherein $Ar^2$ is alkylphenyl.

29. The method of claim 28, wherein $Ar^2$ is methylphenyl.

30. The method of claim 29, wherein $Ar^2$ is p-methylphenyl.

31. The method of claim 20, wherein $Ar^2$ is propylphenyl.

32. The method of claim 31, wherein $Ar^2$ is p-propylphenyl.

33. The method of claim 32, wherein $Ar^2$ is p-isopropylphenyl.

34. The method of claim 13, wherein $Ar^2$ is halo-substituted phenyl.

35. The method of claim 34, wherein $Ar^2$ is p-halo-substituted phenyl.

36. The method of claim 35, wherein $Ar^2$ is p-bromophenyl.

37. The method of claim 36, wherein $Ar^2$ is p-chlorophenyl.

38. The method of claim 13, wherein $Ar^2$ is hydroxyphenyl.

39. The method of claim 38, wherein $Ar^2$ is o-hydroxyphenyl.

40. The method of claim 13, wherein $Ar^2$ is dimethylaminophenyl.

41. The method of claim 40, wherein $Ar^2$ is p-dimethylaminophenyl.

42. The method of claim 12, wherein $Ar^2$ is —$S(O)_2$-substituted aryl.

43. The method of claim 42, wherein $Ar^2$ is 13 $S(O)_2$-substituted phenyl.

44. The method of claim 43, wherein $Ar^2$ is —$S(O)_2$-alkoxyphenyl.

45. The method of claim 44, wherein $Ar^2$ is —$S(O)_2$-methoxyphenyl.

46. The method of claim 45, wherein $Ar^2$ is —$S(O)_2$-p-methoxyphenyl.

47. The method of claim 20, wherein $Ar^2$ is diphenyl.

48. The method of claim 1, wherein compound of Formula I is selected from the group consisting of (4-Methoxy-benzyl)-[1-(4-methoxy-phenyl)-1H-benzimidazol-5-yl]-amine, (4-Dimethylamino-benzyl)-[1-(2-methoxy-phenyl)-1H-benzimidazol-5-yl]-amine, (4-Dimethylamino-benzyl)-(1-phenyl-1H-benzimidazol-5-yl)-amine, (4-Dimethylamino-benzyl)-(1-phenyl-1H-benzimidazol-5-yl)-amine, (4-Bromo-benzyl)-[1-(4-methoxy-phenyl)-1H-benzimidazol-5-yl]-amine, (2-Methoxy-benzyl)-[1-(4-methoxy-phenyl)-1H-benzimidazol-5-yl]-amine, (4-Ethoxy-benzyl)-[1-(4-methoxy-phenyl)-1H-benzimidazol-5-yl]-amine, (2-Methoxy-benzyl)-[1-(2-methoxy-phenyl)-1H-benzimidazol-5-yl]-amine, [1-(4-Methoxy-phenyl)-1H-benzimidazol-5-yl]-naphthalen-1-ylmethyl-amine, (4-Methoxy-benzyl)-(1-p-tolyl-1H-benzimidazol-5-yl)-amine, (4-Chloro-benzyl)-[1-(4-methoxy-phenyl)-1H-benzimidazol-5-yl]-amine, (3,4-Dimethoxy-benzyl)-[1-(4-methoxy-phenyl)-1H-benzimidazol-5-yl]-amine, (4-Bromo-benzyl)-(1-phenyl-1H-benzimidazol-5-yl)-amine, N-(4-Ethoxy-benzyl)-N-[1-(2-methoxy-phenyl)-1H-benzimidazol-5-yl]-4-methylbenzenesulfonamide, [1-(4-Methoxy-phenyl)-1H-benzimidazol-5-yl]-(4-methyl-benzyl)-amine, (2,3-Dimethoxy-benzyl)-[1-(4-methoxy-phenyl)-1H-benzimidazol-5-yl]-amine, (4-Methoxy-benzyl)-[1-(2-methoxy-phenyl)-1H-benzimidazol-5-yl]-amine, (3-Methoxy-benzyl)-[1-(4-methoxy-phenyl)-1Hbenzimidazol-5-yl]-amine, (2,3-Dimethoxy-benzyl)-[1-(2-methoxy-phenyl)-1H-benzimidazol-5-yl]-amine, (4-Isopropyl-benzyl)-[1-(4-methoxy-phenyl)-1H-benzimidazol-5-yl]-amine, (4-Methoxy-benzyl)-(1-phenyl-1H-benzimidazol-5-yl)-amine, N-(4-Isopropyl-benzyl)-N-[1-(4-methoxy-phenyl)-1H-benzimidazol-5-yl]-acetamide, and N-(4-Isopropyl-benzyl)-N-[1-(4-methoxy-phenyl)-1H-benzimidazol-5-yl]-4-methylbenzenesulfonamide.

49. The method of claim 1, wherein the mammal is a human.

50. The method of claim 1, wherein said LCMV-like viruses are selected from the group consisting of Dandenong, Tacaribe, and Pichinde.

51. A method for the treatment of a Junin infection, comprising administering in a therapeutically effective amount to a mammal in need thereof, a compound of Formula I below:

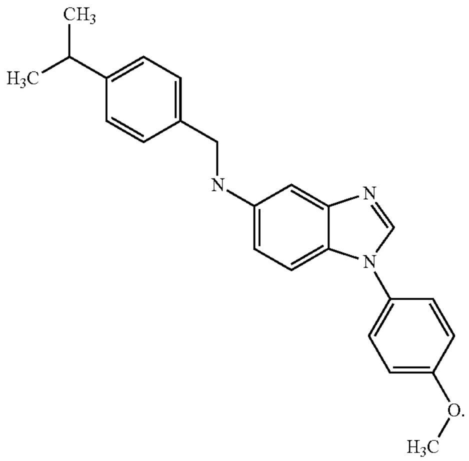

52. The method of claim 51, wherein the mammal is a human.

* * * * *